United States Patent
Dickson et al.

(10) Patent No.: US 8,366,779 B2
(45) Date of Patent: *Feb. 5, 2013

(54) EXPANDABLE IMPLANT, INSTRUMENT, AND METHOD

(75) Inventors: Andrew M. Dickson, Memphis, TN (US); Danny H. Braddock, Jr., Germantown, TN (US); James S. Harrop, Philadelphia, PA (US); Dean G. Karaholios, Lake Forest, IL (US); Eric A. Potts, Indianapolis, IN (US); Christopher I. Shaffrey, Charlottesville, VA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/073,748

(22) Filed: Mar. 28, 2011

(65) Prior Publication Data

US 2011/0172779 A1 Jul. 14, 2011

Related U.S. Application Data

(63) Continuation of application No. 11/412,559, filed on Apr. 27, 2006, now Pat. No. 7,914,581.

(51) Int. Cl.
*A61F 2/44* (2006.01)
(52) U.S. Cl. ............ 623/17.16; 623/17.11; 623/17.15
(58) Field of Classification Search ..... 623/17.11–17.16
See application file for complete search history.

(56) References Cited

U.S. PATENT DOCUMENTS

| | | |
|---|---|---|
| 2,333,033 A | 10/1943 | Mraz |
| 3,701,605 A | 10/1972 | Yoshio |
| 4,157,715 A | 6/1979 | Westerhoff |
| 4,289,123 A | 9/1981 | Dunn |
| 4,386,603 A | 6/1983 | Mayfield |
| 4,401,112 A | 8/1983 | Rezaian |
| 4,553,273 A | 11/1985 | Wu |
| 4,554,914 A | 11/1985 | Kapp et al. |
| 4,599,086 A | 7/1986 | Doty |
| 4,636,217 A | 1/1987 | Ogilvie et al. |
| 4,657,550 A | 4/1987 | Daher |
| 4,892,546 A | 1/1990 | Kotz et al. |
| 5,002,576 A | 3/1991 | Fuhrmann et al. |
| 5,236,460 A | 8/1993 | Barber |
| 5,281,226 A | 1/1994 | Davydov et al. |
| 5,290,312 A | 3/1994 | Kojimoto et al. |
| 5,336,223 A | 8/1994 | Rogers |
| 5,405,391 A | 4/1995 | Hednerson et al. |
| 5,413,602 A | 5/1995 | Metz-Stavenhagen |
| 5,458,641 A | 10/1995 | Ramirez Jimenez |
| 5,480,442 A | 1/1996 | Bertagnoli |
| 5,571,192 A | 11/1996 | Schonhoffer |

(Continued)

FOREIGN PATENT DOCUMENTS

| | | |
|---|---|---|
| DE | 3023942 | 1/1982 |
| DE | 3729600 | 3/1989 |

(Continued)

OTHER PUBLICATIONS

European Patent Office, International Search Report and Written Opinion of PCT/US2007/065845, Sep. 25, 2007, 13 pages.

*Primary Examiner* — Eduardo C Robert
*Assistant Examiner* — Julianna N Harvey

(57) ABSTRACT

Embodiments of the invention include expandable, implantable devices and methods. Devices expand linearly to provide secure fixation between or among anatomical structures. In some embodiments, an implant replaces one or more vertebral bodies of the spine.

20 Claims, 16 Drawing Sheets

U.S. PATENT DOCUMENTS

| | | |
|---|---|---|
| 5,658,335 A | 8/1997 | Allen |
| 5,702,453 A | 12/1997 | Rabbe et al. |
| 5,702,455 A | 12/1997 | Saggar |
| 5,723,013 A | 3/1998 | Jeanson et al. |
| 5,776,197 A | 7/1998 | Rabbe et al. |
| 5,776,198 A | 7/1998 | Rabbe et al. |
| 5,800,547 A | 9/1998 | Schafer et al. |
| 5,916,267 A | 6/1999 | Tienboon |
| 5,989,290 A | 11/1999 | Biedermann et al. |
| 6,015,436 A | 1/2000 | Schonhoffer |
| 6,045,579 A | 4/2000 | Hochshuler et al. |
| 6,080,193 A | 6/2000 | Hochshuler et al. |
| 6,126,660 A | 10/2000 | Dietz |
| 6,176,881 B1 | 1/2001 | Schar et al. |
| 6,190,413 B1 | 2/2001 | Sutcliffe |
| 6,193,755 B1 | 2/2001 | Metz-Stavenhagen et al. |
| 6,193,756 B1 * | 2/2001 | Studer et al. ............... 623/17.15 |
| 6,200,348 B1 | 3/2001 | Biedermann et al. |
| 6,296,665 B1 | 10/2001 | Strand et al. |
| 6,299,644 B1 | 10/2001 | Vanderschot |
| 6,319,257 B1 | 11/2001 | Carignan et al. |
| 6,344,057 B1 | 2/2002 | Rabbe et al. |
| 6,352,556 B1 | 3/2002 | Kretschmer et al. |
| 6,375,683 B1 | 4/2002 | Crozet et al. |
| 6,395,034 B1 | 5/2002 | Suddaby |
| 6,454,806 B1 | 9/2002 | Cohen et al. |
| 6,524,341 B2 | 2/2003 | Lang et al. |
| 6,562,074 B2 | 5/2003 | Gerbec et al. |
| 6,616,695 B1 | 9/2003 | Crozet et al. |
| 6,648,917 B2 | 11/2003 | Gerbec et al. |
| 6,660,038 B2 | 12/2003 | Boyer, II et al. |
| 6,719,796 B2 | 4/2004 | Cohen et al. |
| 6,752,832 B2 | 6/2004 | Neumann |
| 6,783,547 B2 | 8/2004 | Castro |
| 6,866,682 B1 | 3/2005 | An et al. |
| 6,908,485 B2 | 6/2005 | Crozet et al. |
| 2002/0072801 A1 | 6/2002 | Michelson |
| 2002/0082695 A1 | 6/2002 | Neumann |
| 2002/0161441 A1 | 10/2002 | Lang et al. |
| 2003/0045877 A1 | 3/2003 | Yeh |
| 2004/0049271 A1 * | 3/2004 | Biedermann et al. ...... 623/17.11 |
| 2004/0059271 A1 | 3/2004 | Berry |
| 2004/0153160 A1 | 8/2004 | Carrasco |
| 2004/0162618 A1 * | 8/2004 | Mujwid et al. ............ 623/17.15 |
| 2004/0172129 A1 | 9/2004 | Schafer et al. |
| 2004/0181283 A1 | 9/2004 | Boyer, II et al. |
| 2004/0186569 A1 | 9/2004 | Berry |
| 2005/0060036 A1 | 3/2005 | Schultz et al. |
| 2005/0090898 A1 | 4/2005 | Berry et al. |
| 2005/0113921 A1 | 5/2005 | An et al. |
| 2005/0209697 A1 | 9/2005 | Paponneau et al. |
| 2005/0234550 A1 | 10/2005 | Metz-Stavenhagen |
| 2006/0058879 A1 | 3/2006 | Metz-Stavenhagen |
| 2006/0241621 A1 | 10/2006 | Moskowitz |
| 2006/0241770 A1 | 10/2006 | Rhoda |

FOREIGN PATENT DOCUMENTS

| | | |
|---|---|---|
| DE | 4012622 | 7/1991 |
| DE | 9107494 | 10/1991 |
| DE | 4109941 | 10/1992 |
| DE | 4409392 | 9/1995 |
| DE | 4423257 | 1/1996 |
| DE | 19500170 | 2/1996 |
| DE | 19509317 | 9/1996 |
| DE | 19519101 | 11/1996 |
| DE | 19622827 | 12/1997 |
| DE | 29616778 | 3/1998 |
| DE | 19804765 | 8/1999 |
| DE | 20207853 | 5/2002 |
| DE | 20213013 | 1/2003 |
| DE | 10357926 | 9/2005 |
| DE | 20320974 | 2/2007 |
| EP | 0188954 | 7/1986 |
| EP | 0290767 | 11/1988 |
| EP | 0490159 | 6/1992 |
| EP | 0567424 | 10/1993 |
| EP | 0832622 | 4/1998 |
| EP | 0968692 | 1/2000 |
| EP | 1080703 | 3/2001 |
| EP | 1188424 | 3/2002 |
| EP | 1219266 | 7/2002 |
| FR | 2774280 | 1/1998 |
| JP | 62164458 | 7/1997 |
| SU | 1560184 | 4/1990 |
| SU | 1739989 | 6/1992 |
| WO | 9201428 | 2/1992 |
| WO | 9418913 | 9/1994 |
| WO | 9525486 | 9/1995 |
| WO | 9617564 | 6/1996 |
| WO | 9637170 | 11/1996 |
| WO | 9747258 | 12/1997 |
| WO | 9846173 | 10/1998 |
| WO | 9939665 | 8/1999 |
| WO | 9956675 | 11/1999 |
| WO | 9963913 | 12/1999 |
| WO | 0023013 | 4/2000 |
| WO | 0197744 | 6/2001 |
| WO | 0245625 | 6/2002 |
| WO | 03096937 | 11/2003 |
| WO | 2004096103 | 11/2004 |
| WO | 2004100837 | 11/2004 |
| WO | 2005055887 | 6/2005 |

* cited by examiner

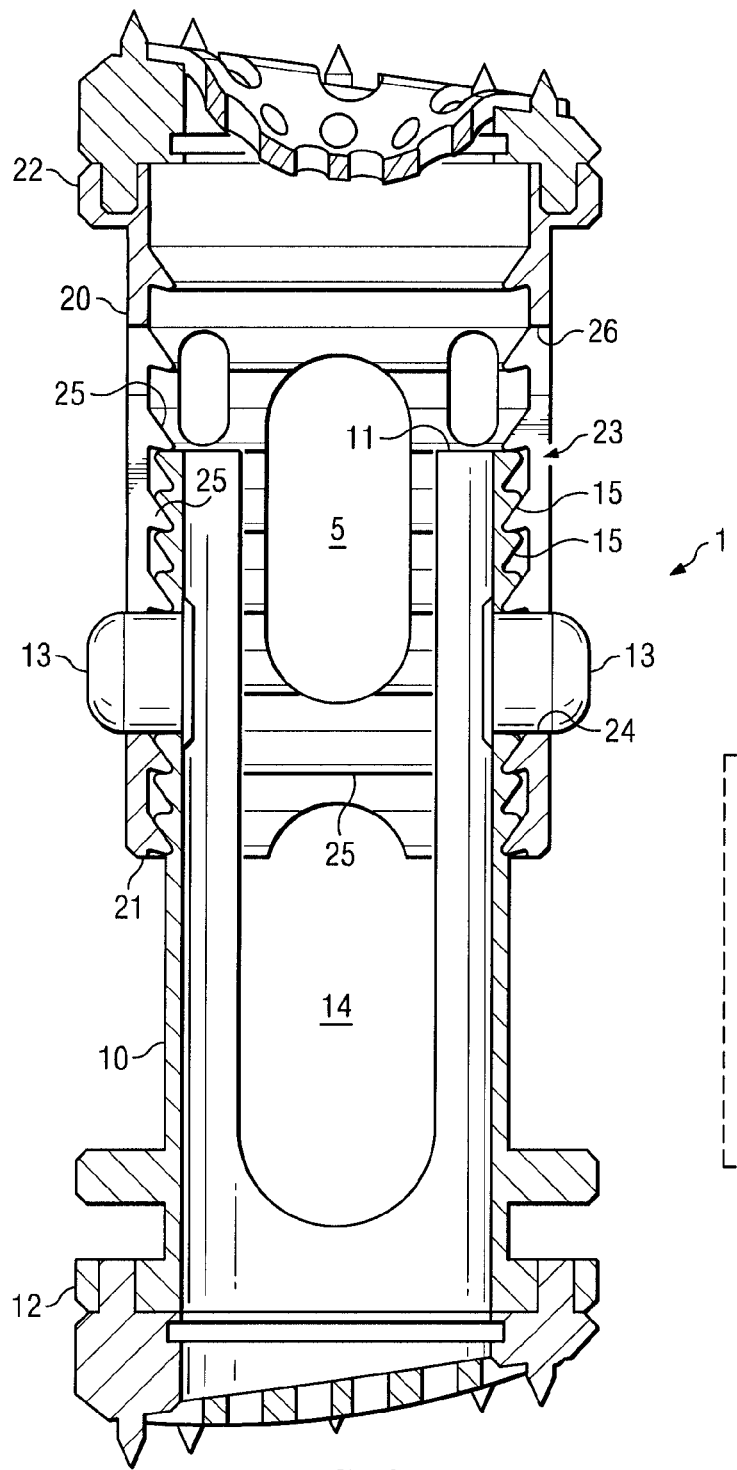
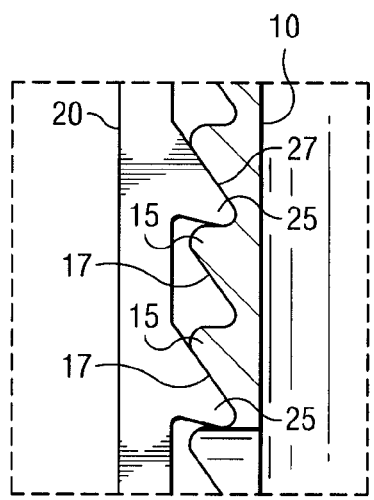
FIG. 3
FIG. 4

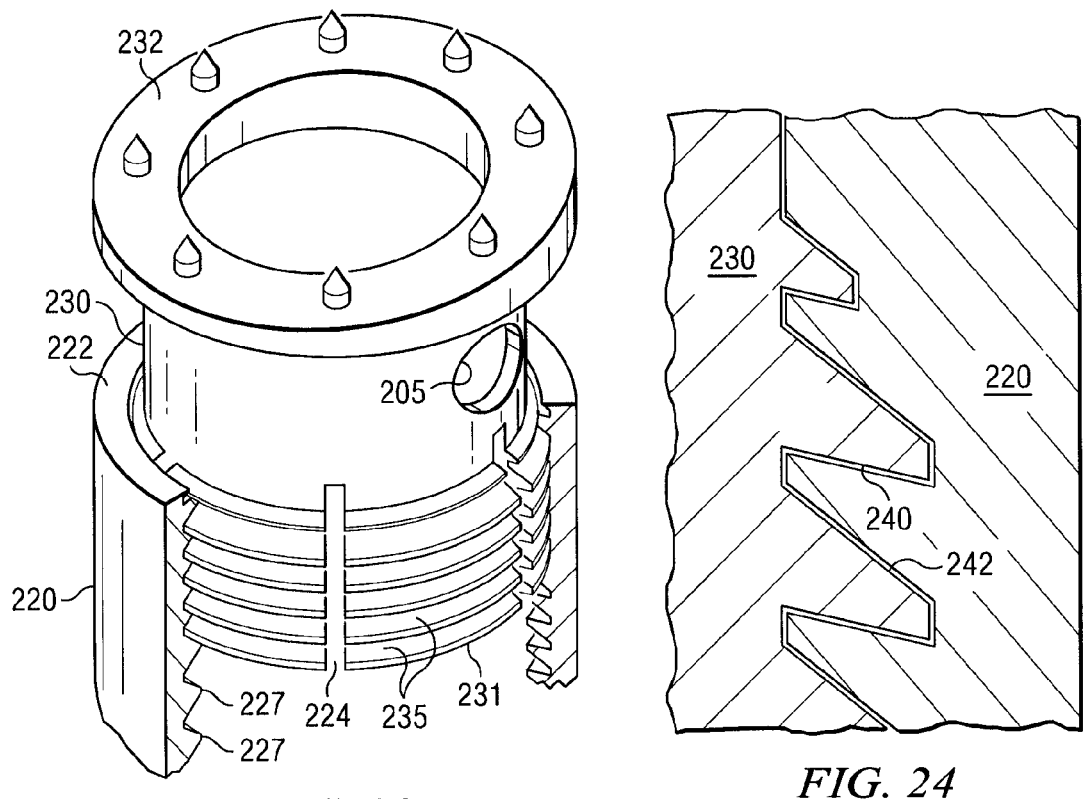
*FIG. 23*  *FIG. 24*
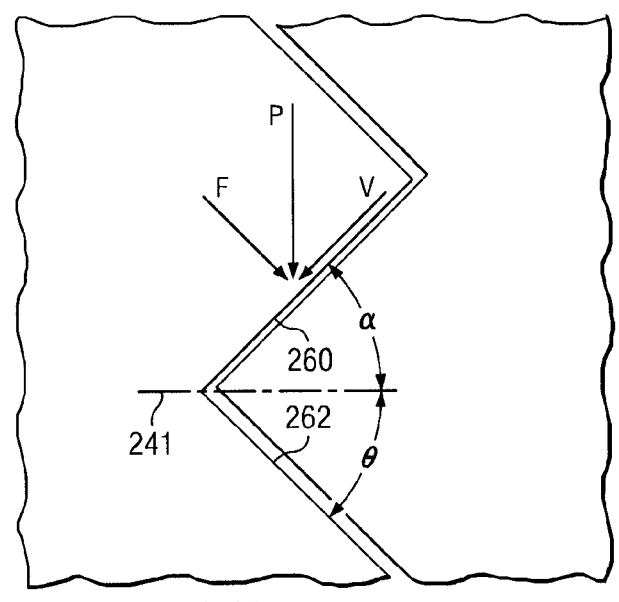
*FIG. 25A*
*(PRIOR ART)*

EXPANDABLE IMPLANT, INSTRUMENT, AND METHOD

CROSS-REFERENCE TO RELATED APPLICATIONS

This application is a Continuation application of U.S. patent application Ser. No. 11/412,559, filed Apr. 27, 2006, now U.S. Pat. No. 7,914,581, the disclosure of which is incorporated herein by reference in its entirety.

FIELD OF THE INVENTION

The present invention relates generally to the field of replacing portions of the human structural anatomy with medical implants, and more particularly relates to an expandable implant and method for replacing skeletal structures such as one or more vertebrae or long bones.

BACKGROUND

It is sometimes necessary to remove one or more vertebrae, or a portion of the vertebrae, from the human spine in response to various pathologies. For example, one or more of the vertebrae may become damaged as a result of tumor growth, or may become damaged by a traumatic or other event. Removal, or excision, of a vertebra may be referred to as a vertebrectomy. Excision of a generally anterior portion, or vertebral body, of the vertebra may be referred to as a corpectomy. An implant is usually placed between the remaining vertebrae to provide structural support for the spine as a part of a corpectomy. FIG. 1 illustrates four vertebrae, $V_1$-$V_4$ of a typical lumbar spine and three spinal discs, $D_1$-$D_3$. As illustrated, $V_3$ is a damaged vertebra and all or a part of $V_3$ could be removed to help stabilize the spine. If removed along with spinal discs $D_2$ and $D_3$, an implant may be placed between vertebrae $V_2$ and $V_4$. Most commonly, the implant inserted between the vertebrae is designed to facilitate fusion between remaining vertebrae. Sometimes the implant is designed to replace the function of the excised vertebra and discs. All or part of more than one vertebrae may be damaged and require removal and replacement in some circumstances.

Many implants are known in the art for use in a corpectomy procedure. One class of implants is sized to directly replace the vertebra or vertebrae that are being replaced. Another class of implants is inserted into the body in a collapsed state and then expanded once properly positioned. Expandable implants may be advantageous because they allow for a smaller incision when properly positioning an implant. Additionally, expandable implants may assist with restoring proper loading to the anatomy and achieving more secure fixation of the implant. Implants that included insertion and expansion mechanisms that are narrowly configured may also provide clinical advantages. In some circumstances, it is desirable to have vertebral endplate contacting surfaces that effectively spread loading across the vertebral endplates. Effective implants should also include a mechanism for securely locking in desired positions, and in some situations, being capable of collapsing. Fusion implants with an uninterrupted opening between their ends may also be advantageous because they allow for vascularization and bone growth through the entire implant.

Expandable implants may also be useful in replacing long bones or portions of appendages such as the legs and arms, or a rib or other bone that is generally longer than it is wide. Examples include, but are not limited to, a femur, tibia, fibula, humerus, radius, ulna, phalanges, clavicle, and any of the ribs.

SUMMARY

One embodiment of the invention is an expandable medical implant for supporting skeletal structures. The implant includes a first tubular member with a connection end and an opposite skeletal interface end, and a second tubular member with a connection end configured to engage with the connection end of the first tubular member, the second tubular member having an opposite skeletal interface end. A key pin is fixed to the first tubular member and positioned in a slot in the second tubular member so that the key pin guides translation between the first tubular member and the second tubular member.

An embodiment of the invention is an expandable medical implant for supporting skeletal structures having a first tubular member with a connection end and an opposite skeletal interface end, and a second tubular member with a connection end configured to engage with the connection end of the first tubular member, the second tubular member having an opposite skeletal interface end. The second tubular member intermittently locks relative to the first tubular member as the implant is expanded. In use in some embodiments, the implant includes an insertion instrument for translating the first tubular member relative to the second tubular member. The insertion instrument has a first tip for attaching to the skeletal interface end of the first tubular member, a second tip for attaching to the skeletal interface end of the second tubular member, and a spreader mechanism for translating the first tip away from the second tip. Moving the first tip toward the second tip results in the first tubular member being released relative to the second tubular member to permit the expandable medical implant to be reduced in length.

Another embodiment of the invention is an end member for a medical implant having a length. The end member is configured to interface with a skeletal structure at the end of the medical implant's length. In some embodiments, the end member includes an end cap with a thickness that provides connection to the medical implant and connection to the skeletal structure, and a shoe for attachment to the end cap. The shoe spans at least a portion of an opening through the end cap, and provides at least in part an interface with the skeletal structure.

An additional embodiment of the invention is a method of placing a medical implant between skeletal structures with an insertion instrument. The method includes accessing a surgical site and expanding the medical implant to fit in a space between skeletal structures by moving at least a portion of the insertion instrument in a first direction. The medical implant progressively locks as expanded. If the locked implant needs to be released from the locked position, the locked implant is released by moving the portion of the insertion instrument in a generally opposite direction.

Yet another embodiment of the invention is an expandable device for supporting skeletal structures. The embodiment includes an implant means for expanding into a space between skeletal structures in a progressively locked state, and an instrument means for expanding the implant into the space by movement of at least a portion of the instrument in a first direction. Movement of the at least a portion of the instrument in a generally opposite direction releases the locked state of the implant.

Another embodiment of the invention is an expandable medical implant for supporting skeletal structures, the medical implant having a length along its expandable dimension.

The implant embodiment includes a first tubular member with a connection end, an opposite skeletal interface end, and a central expansion instrument opening. The implant embodiment also includes a second tubular member with a connection end configured to engage with the connection end of the first tubular member. The second tubular member has an opposite skeletal interface end. Embodiments of the invention include an expansion instrument insertable through the central expansion instrument opening and expandable against the first tubular member and the second tubular member to expand the medical implant. The combined first and second tubular members are of a greater dimension along the length of the implant than the combined first and second tubular members are in any dimension perpendicular to their length.

An embodiment of the invention is a method of placing an expandable vertebral body replacement device that includes making an incision adjacent to a vertebral body, removing at least a portion of the vertebral body, and placing an expandable vertebral body replacement device on an insertion end of a contracted expansion instrument. The contracted expansion instrument is configured to pass through a central portion of the expandable vertebral body replacement device without extending onto any surface of the expandable vertebral body replacement device that is lateral to an insertion direction. The method embodiment also includes inserting the vertebral body replacement device at least in part into a volume left open after removal of the portion of the vertebral body, expanding the expansion instrument to secure the vertebral body replacement device, and removing the expansion instrument through the incision.

Another embodiment of the invention is a device for supporting skeletal structures having an expandable implant with a first tubular member and a second tubular member and having a means for receiving an expansion instrument, and an expansion instrument means for expanding against the first tubular member and the second tubular member to expand the medical implant. The expansion instrument means is centrally located on the expandable implant such that when the expandable implant is placed in a person to support the skeletal structures with the expansion instrument means attached, ends and lateral extents of the expandable implant are viewable from the direction of insertion of the implant.

An embodiment of the invention is an expandable medical implant with a length along its expandable dimension. The medical implant is for supporting skeletal structures. The implant includes a first tubular member with a connection end having a first set of protrusions and an opposite skeletal interface end. The implant embodiment includes a second tubular member with a connection end including a second set of protrusions configured to engage with the connection end of the first tubular member, the second tubular member including an opposite end opposite from the connection end. The first set of protrusions includes a flank with a negative flank angle. The flank is positively loaded when the implant is compressively loaded along its length.

Another embodiment of the invention is an expandable medical implant with a length along its expandable dimension. The medical implant is for supporting skeletal structures and includes a first tubular member with a connection end having a first set of protrusions and an opposite skeletal interface end. The implant also includes a second tubular member with a connection end having a second set of protrusions configured to engage with the connection end of the first tubular member. The second tubular member has an opposite end opposite from the connection end. Compressively loading the implant along its length generates a compressive force between the first and second tubular member transverse to the length of the implant. This force tends to more securely engage the first and second sets of protrusions.

Yet another embodiment of the invention is an expandable medical implant with a length along its expandable dimension, the medical implant for supporting skeletal structures. The embodiment of the implant includes a first tubular member with a connection means, a second tubular member with a connections means for coupling with the first tubular member, means for translating the first tubular member relative to the second tubular member to provide coarse expansion adjustment, and means for providing fine length adjustment by turning the second tubular member relative to the first tubular member.

Still another embodiment of the invention is a method of implanting an expandable medical implant with a length along the expandable dimension of the implant. The method embodiment includes the acts of pulling a first tubular member with a first set of threads away from a second tubular member with a second set of threads, causing the first and second sets of threads to translate relative to one another along the length of the implant, and turning the second tubular member relative to the first tubular member to adjust the expanded length of the medical implant.

An embodiment of the invention is a method of implanting an expandable medical implant with a length along the expandable dimension of the implant. The embodiment includes the act of pulling a first tubular member with a first set of right-hand threads away from a third tubular member with a fourth set of left-hand threads. The medical implant comprising a second tubular member with a second set of right-hand threads and a third set of left-hand threads, the act of pulling causing the first and second sets of threads to translate relative to one another along the length of the implant and the third and fourth sets of threads to translate relative to one another along the length of the implant. An additional act of the embodiment is turning the second tubular member relative to the first and third tubular members to adjust the expanded length of the medical implant.

BRIEF DESCRIPTION OF THE DRAWINGS

FIG. 3 is side cross-sectional view of the implant of FIG. 2.
FIG. 4 is an enlarged view of a portion of the implant illustrated in FIG. 3.

FIG. 23 is perspective view of the superior end of the implant of FIG. 21 with a partially cut away section.

FIG. 24 is an enlarged perspective view of the superior end of the implant of FIG. 21.

FIG. 25A is a cross-sectional view of a prior art thread profile.

DETAILED DESCRIPTION

Figure 1:
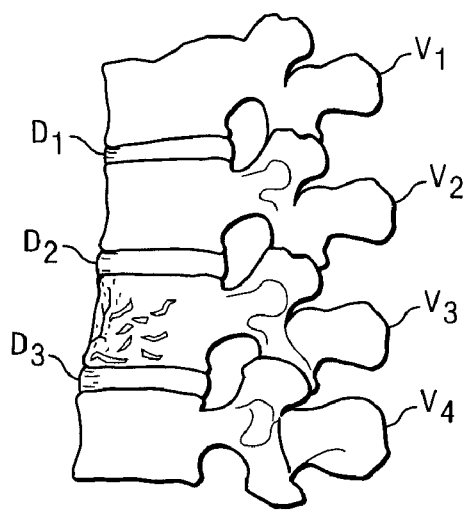
FIG. 1 is an elevation view of a segment of a lumbar spine.

FIGS. 2-5 illustrate an expandable medical implant 1 for supporting skeletal structures. In the illustrated embodiment, the medical implant 1 includes a first tubular member 10 with a connection end 11 and opposite first skeletal interface end 12, and a second tubular member 20 with a connection end 21 configured to engage with the connection end 11 of the first tubular member 10. The second tubular member 20 has an opposite second skeletal interface end 22. A key pin 13 is fixed to the first tubular member 10 and positioned in a slot 23 in the second tubular member 20 such that the key pin 13 guides translation between the first tubular member 10 and the second tubular member 20. The embodiment shown includes a medial aperture 5 through which bone growth material may be packed and through which bone growth may occur. Additionally, the medial aperture 5 is an aid in radiographic assessment when the implant 1 is made from a material that is not radiolucent. Openings 6 are also useful for packing of bone growth material, and provide channels through which bone growth may occur.

Figure 2:
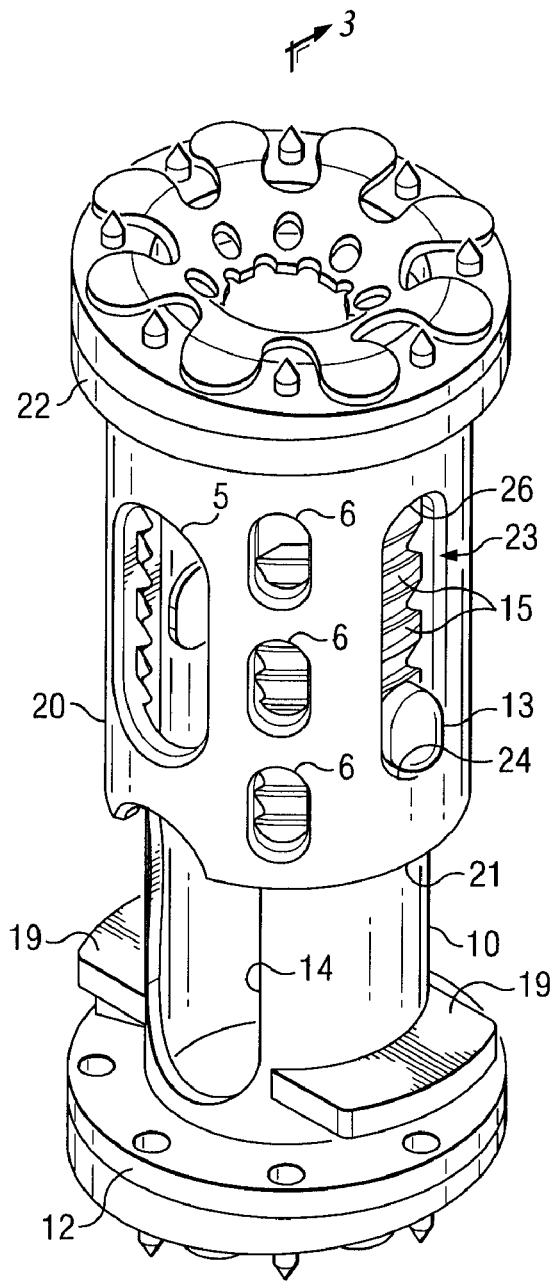
FIG. 2 is a perspective view of an expandable implant.

The term tubular as used herein includes generally cylindrical members as are illustrated in FIG. 2, but may also include other enclosed or partially enclosed cross-sectional shapes. By way of example and without limitation, tubular includes fully or partially, cylindrical, elliptical, rectangular, square, triangular, semi-circular, polygonal, and other cross-sectional shapes of these general types.

The illustrated key pin 13 guides the translation of the first and second tubular members 10, 20 and provides torsional stability between the tubular members 10, 20. In addition, as shown in FIG. 2, the key pin 13 provides a positive stop to the expansion of the medical implant 1 by limiting the travel of the second tubular member 20 with interference between the key pin 13 and the bottom 24 of the slot 23. Similarly, the key pin 13 provides a positive stop to the contraction of the medical implant 1 by limiting the travel of the second tubular member 20 with an interference between the key pin 13 and the top 26 of the slot 23. As will be described in more detail below, the key pin 13 also provides a connection interface between an insertion instrument and the first tubular member 10.

As shown in the illustrated embodiment, the first tubular member 10 fits within the second tubular member 20. However, in other embodiments, the first tubular member may be of greater diameter than the second tubular member with the connection between the two members being reversed in orientation. Alternatively, the first and second tubular members may be of approximately the same size, but have legs that exist coplanarly or within the same tubular geometry with the legs of the other.

Figure 5:
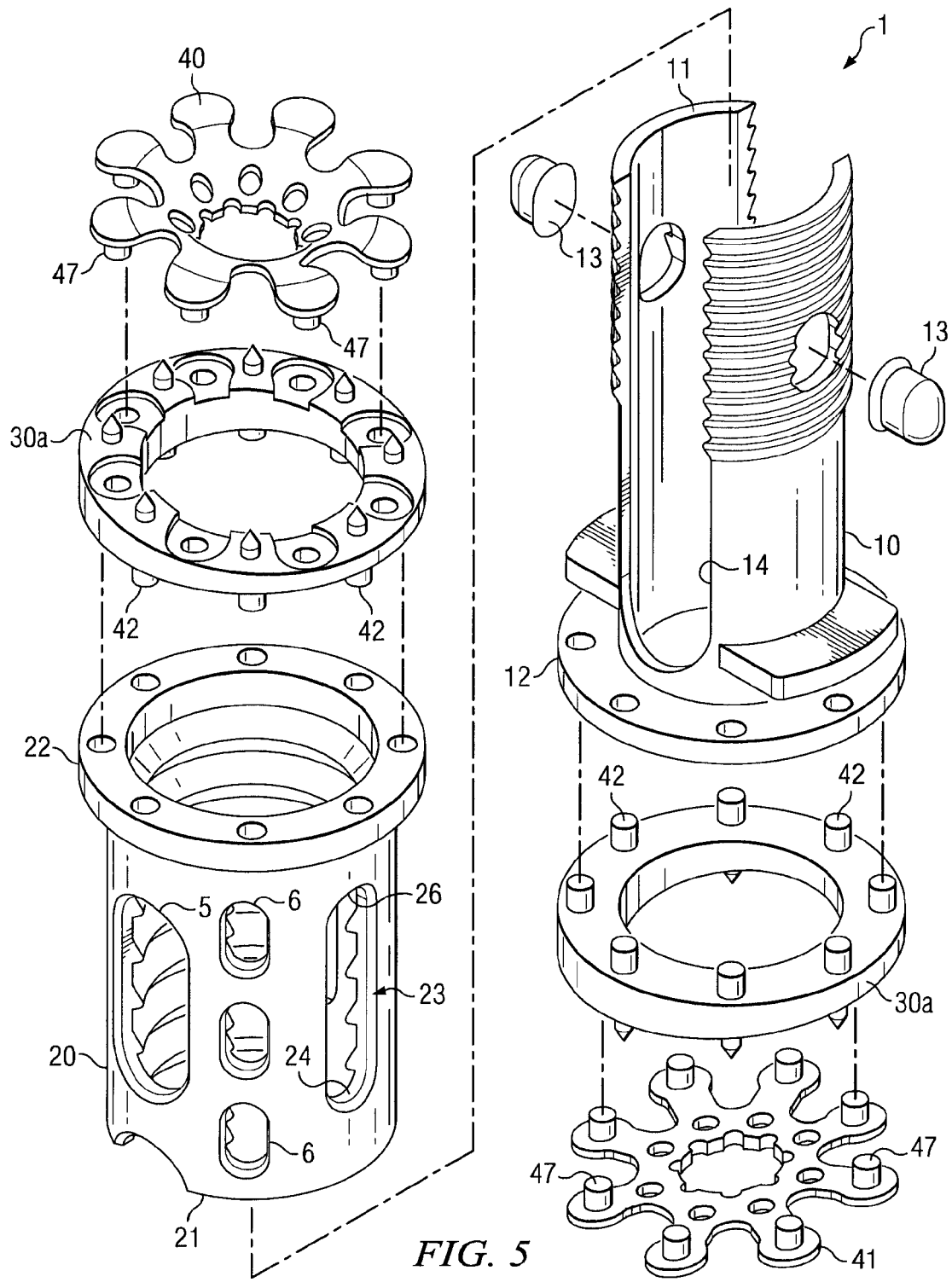
FIG. 5 is an exploded view of the implant of FIG. 2.

As shown in FIGS. 2, 3, and 5, the first tubular member 10 includes a relief cut 14 to facilitate portions of the first tubular member 10 flexing away from the second tubular member 20 to permit translation between the first and second tubular members. The flexing may be induced by pulling the first tubular member 10 away from the second tubular member 20 to expand the medical implant 1. Referring now to FIG. 4, pulling the first tubular member 10 down while pulling the second tubular member 20 up causes the inclined first flank 17 of the first protrusions, or first set of teeth 15, to press against the second flank 27 of the second protrusions, or second set of teeth 25. Because the second tubular member 20 has a continuous cross-section, it has a relatively stronger lateral resistance than the first tubular member 10 with its relief cut 14. Therefore, the force induced between the first and second flanks, 17, 27, causes the first tubular member 10 to flex away from the second tubular member 20. In other embodiments, a relief cut in the second tubular member 20 and a continuous shape in the first tubular member 10 could cause flexing of the second tubular member rather than the first. The degree and direction of flexing can be controlled by the use of different materials, various degrees of relief cutting, different cross-sectional shapes, and the shapes of the teeth or protrusions employed, among other factors. The force required for various degrees of flexing of the members is proportional to the force required to expand the implant. Therefore, the force required to expand the implant may be maintained within a desirable range by controlling the factors detailed above.

As best illustrated in FIGS. 3 and 4, the first tubular member 10 includes a set of first teeth 15, or more generally, protrusions, wherein the rows of teeth are adjacent to one another. The second tubular member 20 includes a set of second teeth 25, or more generally, protrusions, wherein the rows of teeth are not adjacent to one another. As shown, every other row of the set of second teeth 25 has been removed. However, in other embodiments, every third or fourth or some other number of rows may contain teeth, or the tooth pattern may repeat in some non-uniform fashion. If the sets of teeth were threads instead, a similar effect could be achieved by widening the pitch of the threads on one of the tubular members.

The first set of teeth 15 interdigitate with every other one of the teeth of the set of second teeth 25. This or other varied spacings may be advantageous. As noted above, the force required to expand the implant is proportional to the number of sets of teeth that are in contact while the tubular members 10, 20 are being translated. However, if teeth on both tubular members 10, 20 are spaced apart at greater distances, the number of increments to which the implant may be adjusted is decreased. By maintaining the frequency of the rows of the first set of teeth 15 and increasing frequency of the second set of teeth 25, the force required to expand the implant is reduced, but the number of discrete points of adjustment is not reduced. In some embodiments, the increased frequency of teeth could be maintained on the second tubular member 20 while the spacing is increased on the first tubular member 10.

Figure 6:
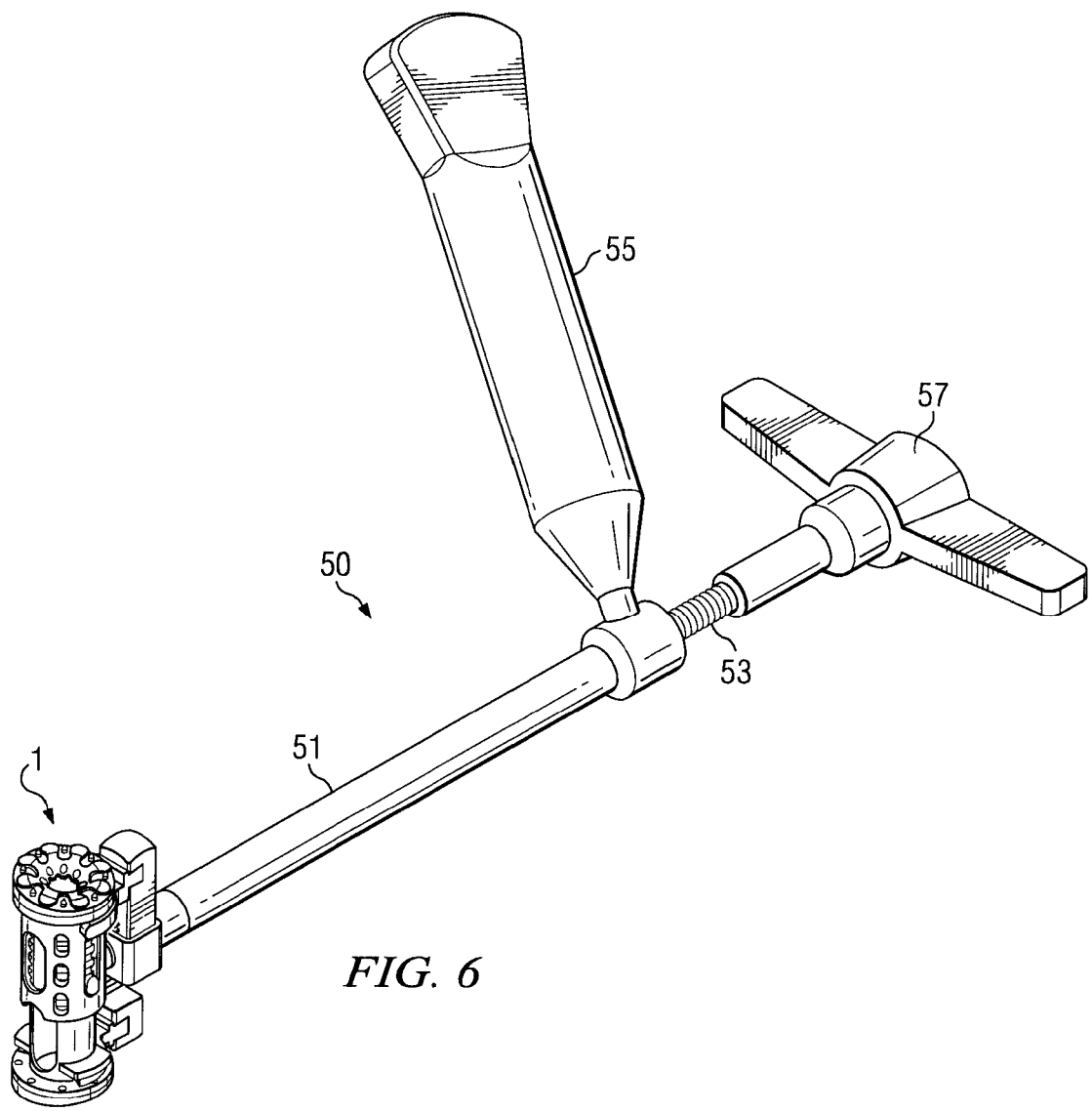
FIG. 6 is a perspective view of the implant of FIG. 2 and an attached instrument.

FIG. 6 illustrates an insertion instrument 50 for expanding the implant 1. The insertion instrument 50 includes an outer shaft 51 and in inner shaft 53 disposed within the inner shaft 51. A counter-torque handle 55 is coupled to the outer shaft 51. A drive handle 57 is coupled to the proximal end of the inner shaft 53. A rack and pinion assembly 60 is coupled to the distal end of the outer shaft 51 and the inner shaft 53.

Figure 7:
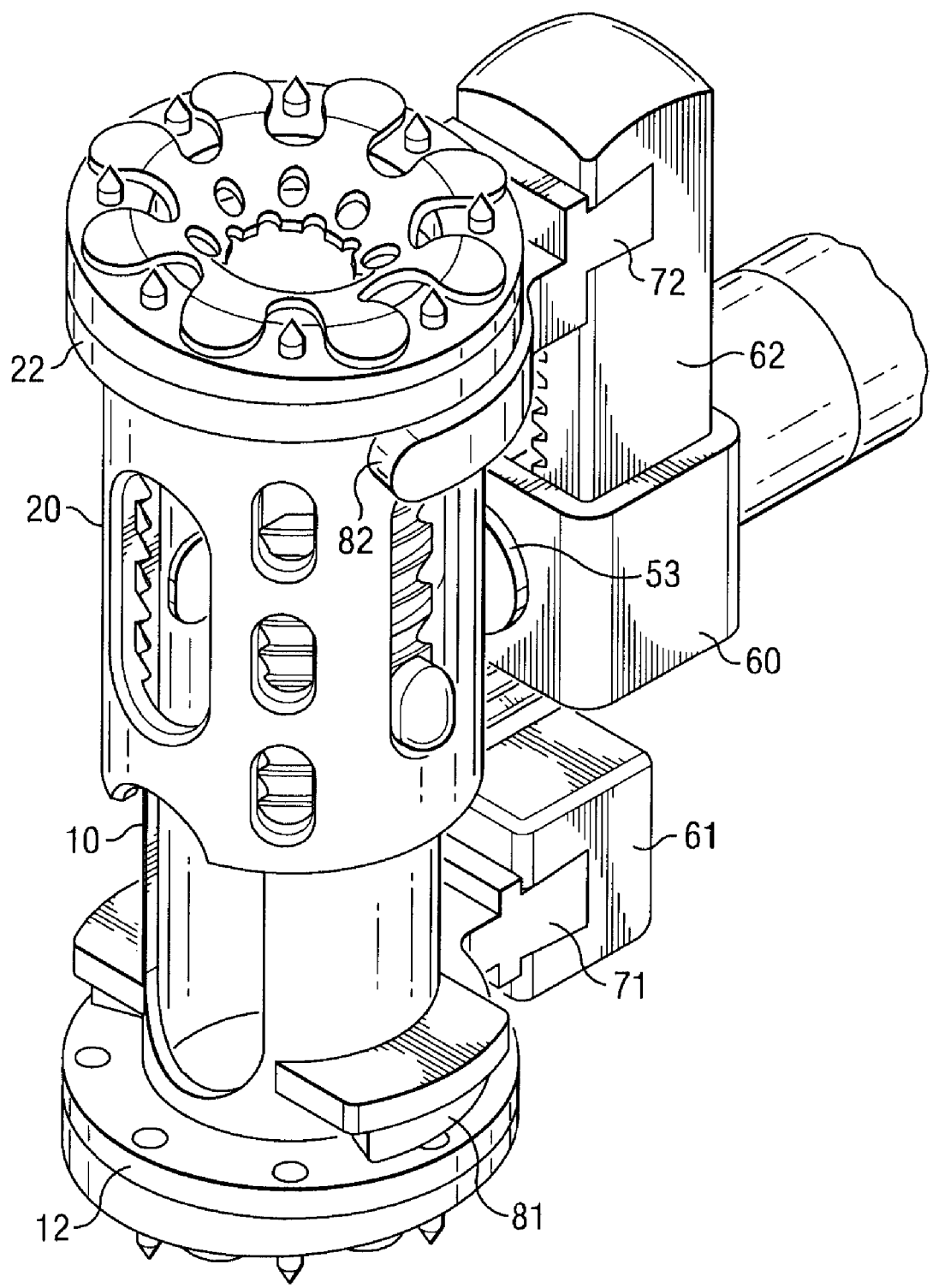
FIG. 7 is an enlarged perspective view of the implant of FIG. 2 and a portion of an attached instrument.

Referring now to FIG. 7, the rack and pinion assembly 60 includes a lower rack 61 and an upper rack 62 along with a pinion (not shown), which is disposed on the end of the inner shaft 53. The lower rack 61 has a first socket 71 for receiving a first tip 81. The first tip 81 connects to the first tubular member 10 near the first skeletal interface end 12. As illustrated, two retainers 19 prevent the first tip 81 from moving along the implant away from the first skeletal interface end 12. The upper rack 62 has a second socket 72 for receiving a second tip 82. The second tip 82 connects to the second tubular member 20 near the second skeletal interface end 22. The second tubular member 20 of the illustrated embodiment does not have any mechanism for restricting the movement of the second tip 82 away for the second skeletal interface end 22.

When the drive handle 57 is rotated in a clockwise direction, the inner shaft 53 actuates the rack and pinion assembly, spreading the first and second tips 81, 82, and expanding the implant 1. Other embodiments of the insertion instrument 50 may operate by motions other than turning of a handle or knob, or may expand as a result of counter-clockwise rotation. For example and without limitation, the spreading motion may be created by a linkage system such as pliers, by a ratcheting or screw-driven jack, by pull or push grip handles, or by pneumatic or electric actuators. The alternative mechanisms may be reversible or two separate instruments may be used to expand and compress the tips of the instrument. Instruments such as those disclosed in U.S. patent application Ser. No. 10/441,689, entitled "Instruments and Techniques for Separating Bony Structures," filed May 20, 2003; and U.S. patent application Ser. No. 11/291,419, entitled "End Device for a Vertebral Implant," filed Dec. 1, 2005 may be used in embodiments of the invention and these applications are hereby incorporated by reference in their entirety. In some embodiments, the rack and pinion assembly 60 is offset laterally from the outer shaft to provide direct visualization of the implant in the surgical site. Instruments of any of these varieties may be used as part of or in combination with implants 1, 1a, 100, and 200, specifically disclosed herein or as otherwise effectively applied.

The implant 1 of the illustrated embodiment progressively locks as expanded. The expansion may also be described as intermittent since locking occurs at the discrete locations where teeth from the first and second sets of protrusions align.

Figure 8:
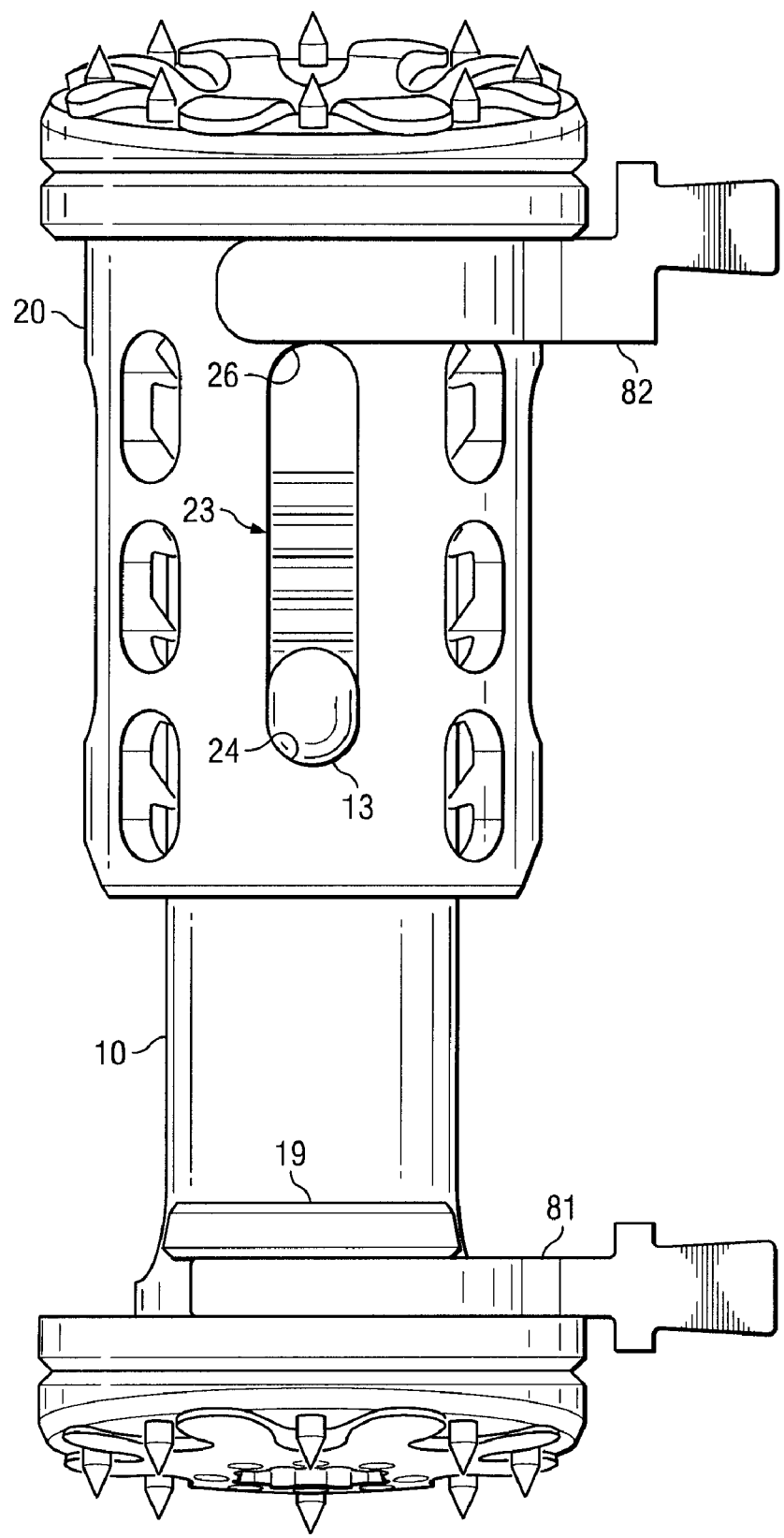
FIG. 8 is an elevation view of the implant of FIG. 2 and a portion of an attached instrument in an expanded state.
Figure 9:
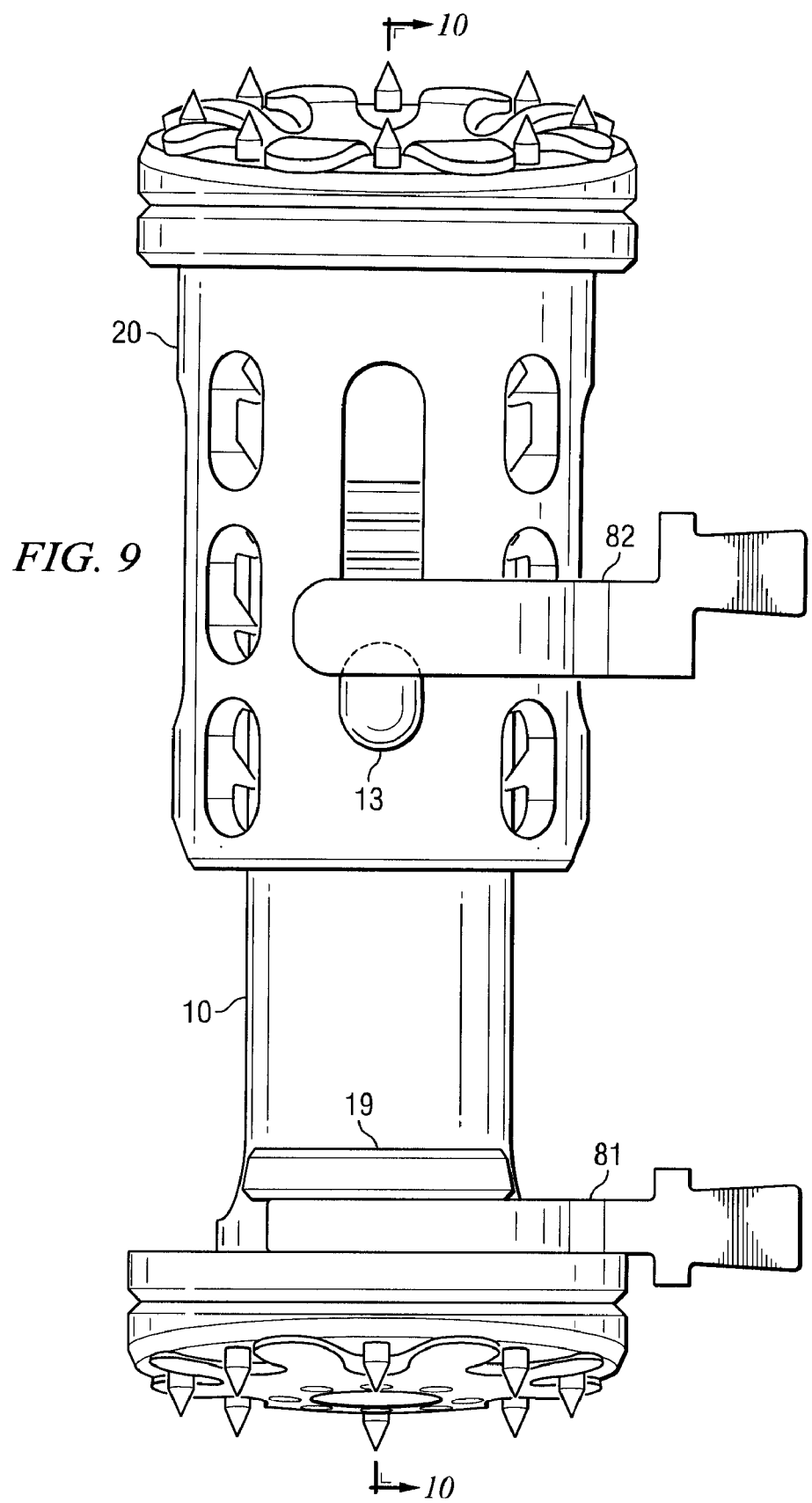
FIG. 9 is an elevation view of the implant of FIG. 2 and a portion of an attached instrument in an expanded state, and with the instrument positioned to release the implant for collapsing.
Figure 10:
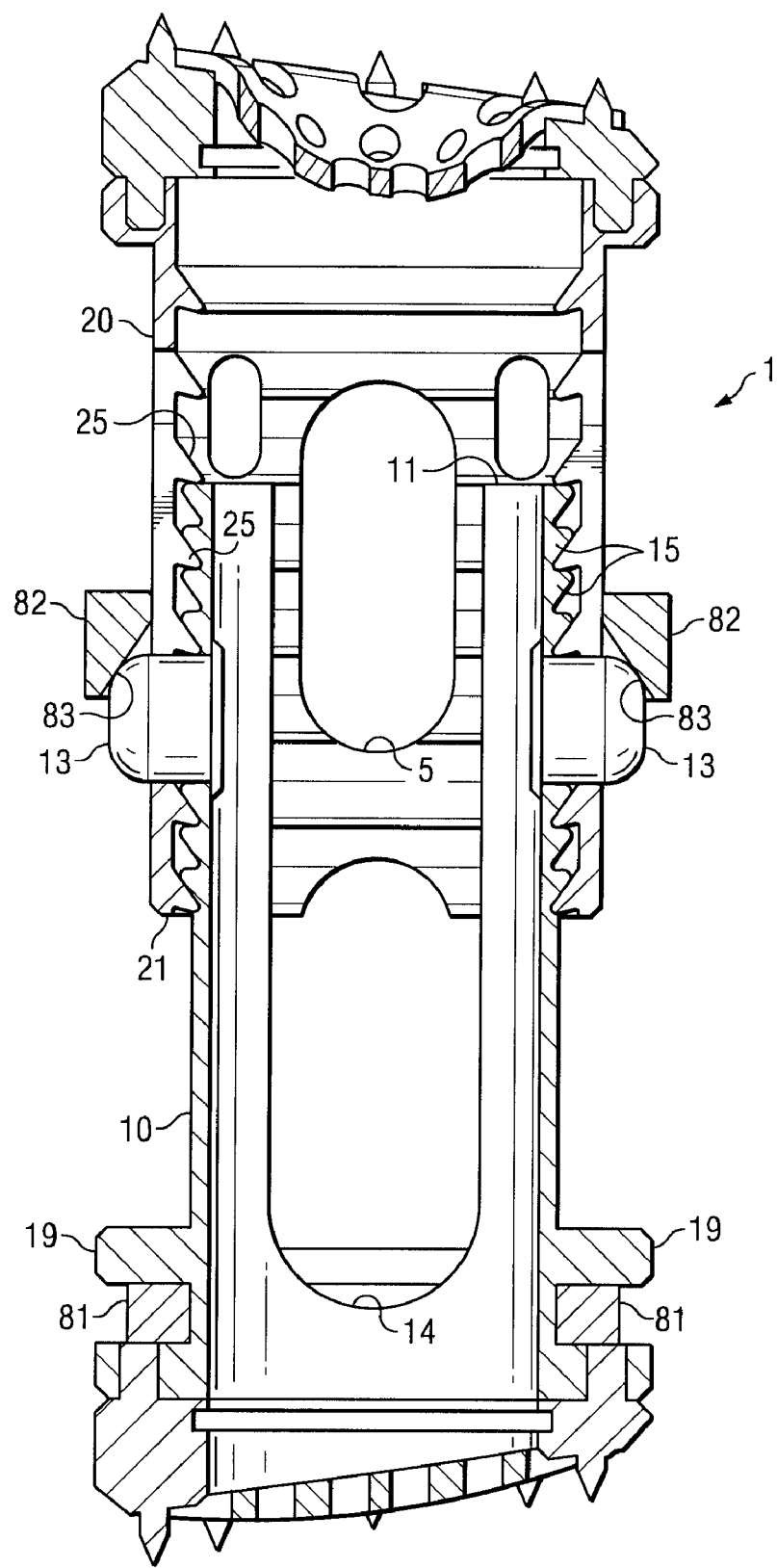
FIG. 10 is a side cross-sectional view of the implant and instrument of FIG. 9.

FIGS. 8-10 illustrate the implant 1 being expanded and then released by the first and second tips 81, 82 of the insertion instrument 50. FIG. 8 shows the implant in a fully expanded condition with the key pins 13 contacting the bottom 24 of the slot 23. In FIGS. 9 and 10, the first and second tips 81, 82 have been contracted to apply a force to the key pins 13. In the illustrations, the second tip 82 is in position to apply a flexing force to the key pins 13, but has not yet applied sufficient force for the key pins 13 to be moved inwardly. The first and second tips 81, 82 are drawn together by turning the drive handle 57 in a counter-clockwise direction in this embodiment. Two retainers 19 prevent the first tip 81 from moving along the implant 1 away from the first skeletal interface end 12, but the second tip 82 is able to move away from the second skeletal interface end 22 to contact the key pins 13. In some embodiments, the second tip 82 includes at least one capture mechanism 83 for engaging a portion of one or more of the key pins 13. Because the capture mechanism 83 and the key pin 13 make contact along an inclined surface, downward motion of the second tip 82 causes the key pin 13, and thus the first tubular member 10, to flex inwardly. Inward flexing of the first tubular member 10 disengages the first set of teeth 15 from the second set of teeth 25 and releases locking between the first and second tubular members 10, 20.

In addition to releasing locking, the capture mechanism 83 enables a secure temporary connection to the implant 1 by the insertion instrument 50. With the implant 1 held in the insertion instrument 50, the implant 1 may be positioned, repositioned, or removed from the surgical site. In other embodiments, a capture mechanism may be a feature of the first tip 81. In such embodiments, release of the locking may be keyed to force or motion from an action delivered through the first tip 81.

The insertion instrument 50 in combination with the first and second tubular members 10, 20 provides a significant clinical advantage in some embodiments. The combination enables insertion, expansion, locking, and contraction without the need for exchanging instruments or adding additional pieces to the device. The illustrated implant 1 automatically locks as expanded. The insertion instrument 50 is capable of holding, expanding, contracting, and repositioning the implant 1 without ever being removed from the surgical site.

Generally stated, the insertion instrument 50 in combination with the implant 1 is an expandable skeletal structure support device that progressively locks as expanded. Movement of at least a portion of the instrument in a first direction generates the expansion, and generally opposite movement releases the locked state of the implant 1.

In practice, an implant such as the implant 1 is placed between skeletal structures by first accessing the surgical site. Access may be through any surgical approach that will allow adequate visualization and/or manipulation of the skeletal structures. Example surgical approaches include, but are not limited to, any one or combination of anterior, antero-lateral, posterior, postero-lateral, transforaminal, and/or far lateral approaches. Implant insertion can occur through a single pathway or through multiple pathways, or through multiple pathways to multiple levels of the spinal column. Minimally invasive techniques employing instruments and implants are also contemplated. Similar approaches and pathway are applicable to implants 100 and 200.

With access established, the medical implant 1 is placed and expanded to fit in a space between skeletal structures. It is often necessary to further open or prepare the space between skeletal structures, which can be done by any technique available to the surgeon. Expansion of the implant 1 may be carried out by moving at least a portion of the insertion instrument 50 in a first direction, as detailed herein. Embodiments of the implant 1 progressively lock as expanded by the insertion instrument 50. In some circumstances, it is desirable to release the implant 1 from its locked state. For example, upon initial placement and assessment under fluoroscopy, a determination may be made that the implant 1 is not appropriately placed or sized. As described in detail in association with FIGS. 9 and 10, generally opposite motion of a portion of the insertion instrument 50 releases the locked implant.

Figure 14A:
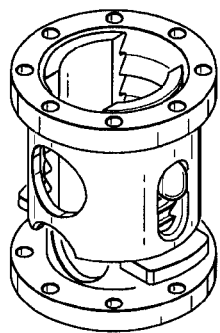
FIGS. 14A and 14B are perspective views of implants embodiments of varying sizes.
Figure 14B:
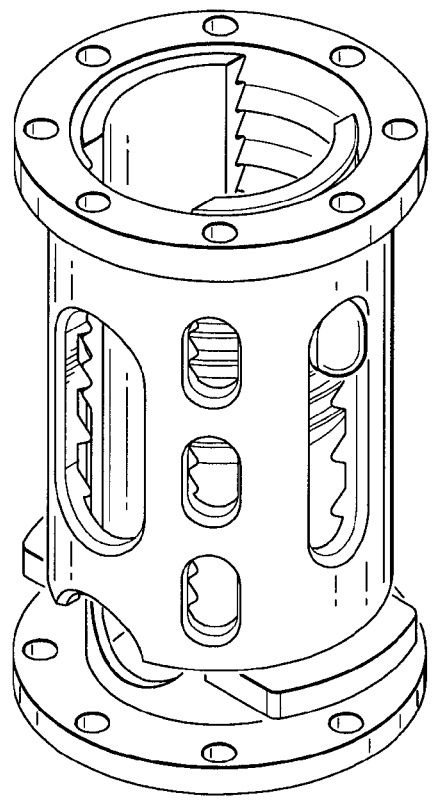

FIGS. 14A and 14B show a range of implant sizes that may be useful in a clinical setting. The implant in FIG. 14A is approximately 13 mm in diameter and may range from approximately 16 mm to 20 mm in height. The implant in FIG. 14B is approximately 25 mm in diameter and may range from approximately 50 mm to 65 mm in height. These are not limiting sizes for the disclosed implants, but are only examples of various sizes. As is evident from the variation in size, a conventional, single insertion instrument 50 would not have an appropriate grasping mechanism to secure, expand, and insert all instrument sizes. However, embodiments of the present invention include tip mechanisms for inserting implants of various sizes. As illustrated in FIG. 7, the lower rack 61 has a first socket 71 for receiving a first tip 81. The first tip 81 connects to the first tubular member 10 near the first skeletal interface end 12. The upper rack 62 has a second socket 72 for receiving a second tip 82. The second tip 82 connects to the second tubular member 20 near the second skeletal interface end 22. Embodiments of the invention include a set of two or more variously sized first interchangeable tips that may be placed in the first socket 71 one at a time to accommodate first tubular members 10 of different, matching sizes. Likewise, embodiments also include a set of two or more variously sized second interchangeable tips that may be placed in the second socket 72 one at a time to accommodate second tubular members 20 of different, matching sizes. First and second interchangeable tips may be used in any combination to accommodate respective tubular member pieces.

Figure 16:
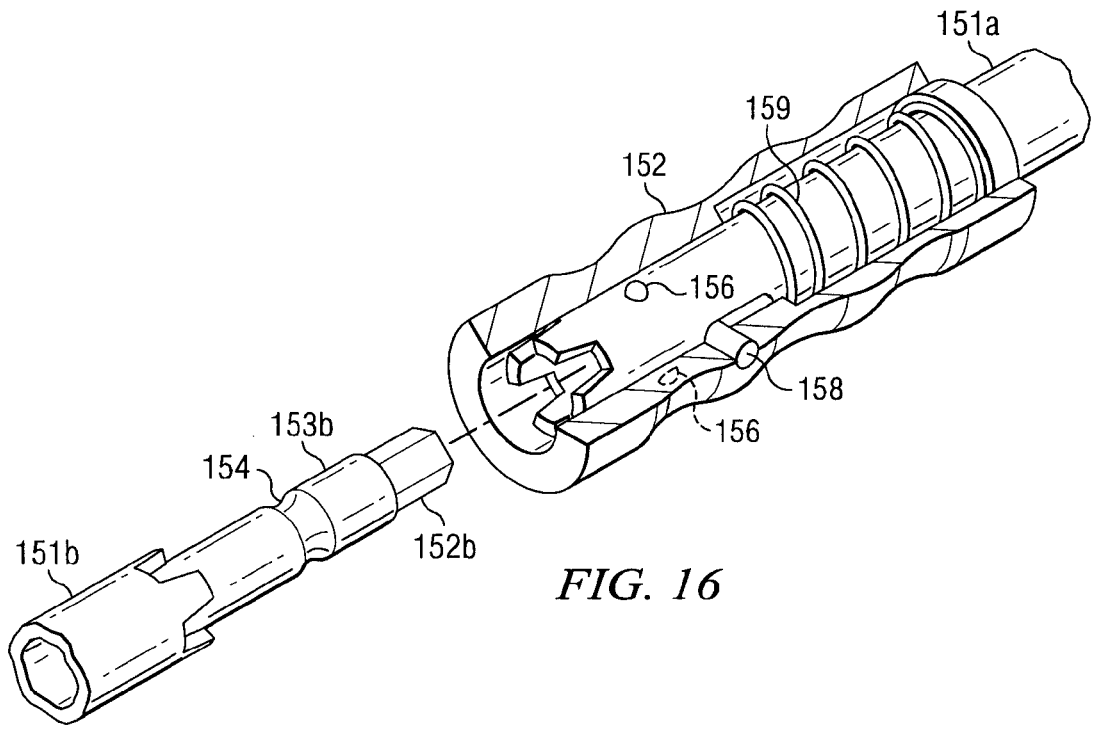
FIG. 16 is a partially exploded perspective view of a connection within the modular instrument of FIG. 15.
Figure 15:
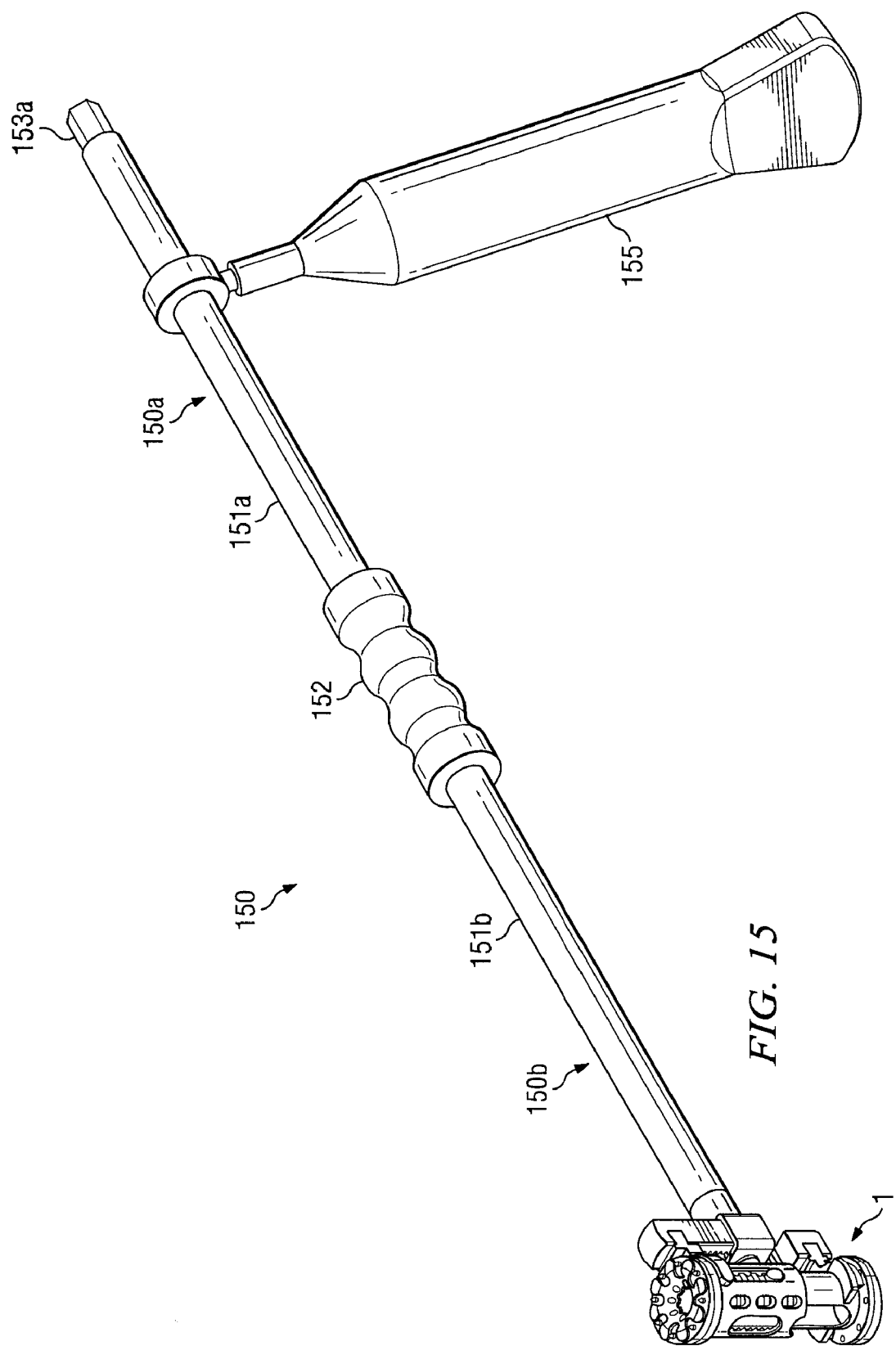
FIG. 15 is a perspective view of an implant embodiment attached to a modular embodiment of an instrument.

FIGS. 15 and 16 illustrate an embodiment of an insertion instrument that is configured to provide modular rack and pinion assemblies that match implants. Rather than, or in addition to, sets of tips to match implant sizes, the modular insertion instrument 150 provides for a set of distal components 150*b* that fit a set of variously sized implants 1. The various distal components 150*b* match a standard torque base 150*a* that couples to the distal component 150*b* and applies torque to the component. The standard torque base 150*a* includes a proximal inner torque shaft 153*a*, a proximal outer torque shaft 151*a* disposed about the proximal inner torque shaft 153*a*, and an adjustable counter torque handle 155. The adjustable counter torque handle 155 may be loosened, positioned at any radial angle about standard torque base 150*a*, tightened, and used to hold the proximal outer torque shaft 151*a* steady while applying torque to the proximal inner torque shaft 153*a*. A torque handle of any effective type may be applied to the end of the proximal inner torque shaft 153*a* to turn the shaft.

Each distal component 150*b* includes a distal outer torque shaft 151*b* and a distal inner torque shaft 153*b*. The distal inner torque shaft 153*b* has a distal inner torque coupling 152*b* and a retaining notch 154. The distal inner torque coupling 152*b* fits in a corresponding proximal inner torque coupling (not shown) to transfer torque from the proximal inner torque shaft 153*a* to the distal inner torque shaft 153*b*. The retaining notch 154 is configured to receive one or more detent balls 156 to restrict movement of the distal component 150*b* away from the proximal component 150*a*. The proximal outer torque shaft 151*a* and the distal outer torque shaft 151*b* also couple through a torque fitting. A coupling sleeve 152 is disposed over the outer torque shafts 151*a*, 151*b* to maintain their alignment and to keep the detent balls 156 engaged in the retaining notch 154. The coupling sleeve 152 is maintained in a predetermined range by attachment to retaining pin 158. A retaining spring 159 keeps the coupling sleeve 152 biased over the joint between the outer torque shafts 151*a*, 151*b*.

In operation, to load a distal component 150*b* into the proximal component 150*a*, the coupling sleeve 152 is pulled proximally, and the distal component 150*b* is inserted into the proximal component 150*a*. The coupling sleeve is allowed to slide over the joint between the components, and the instrument is ready for use. To remove the distal component 150*b*, the coupling sleeve 152 is pulled proximally and the distal component 150*b* is removed from the proximal component. Similarly, various distal components with differently sized implants may be coupled to the proximal component 150*a*.

Figure 11:
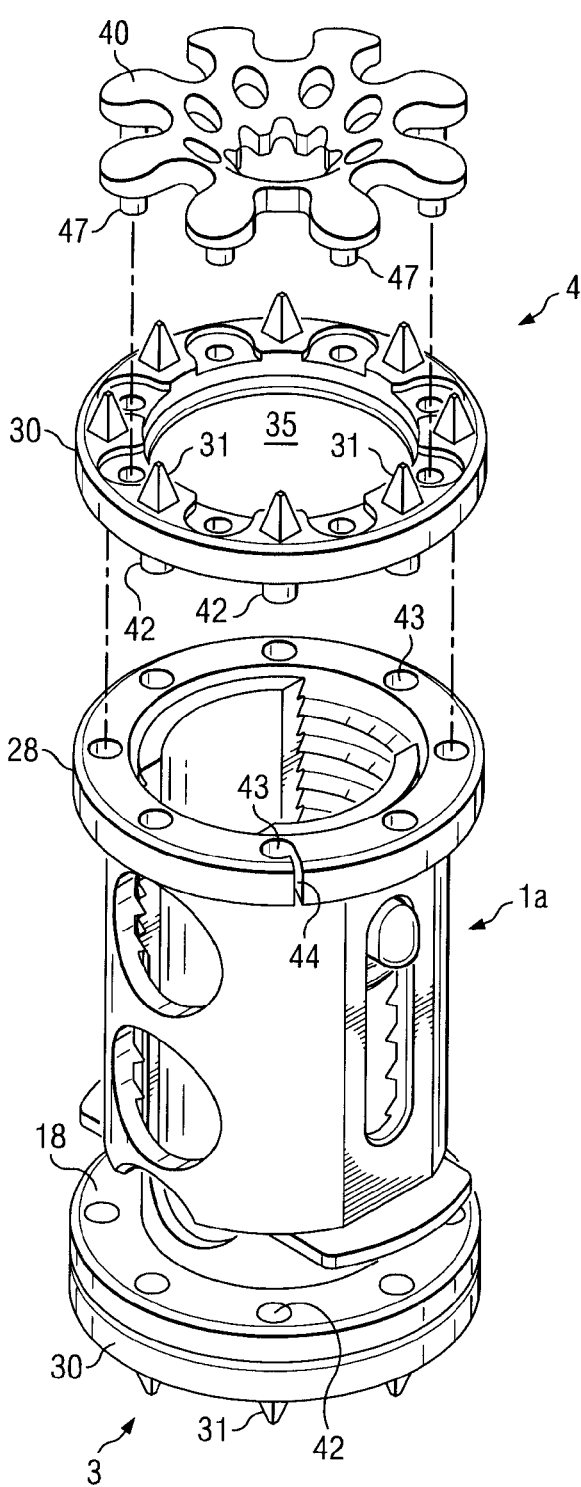
FIG. 11 is a partially exploded perspective view of an embodiment of the implant.

FIG. 11 shows an inferior end member 3 and a superior end member 4 coupled to and in an exploded view relationship with a medical implant 1*a*. As illustrated, the medical implant 1*a* is a corpectomy device, but could in other embodiments be a device for positioning within a long bone or other structure. The end members 3, 4 could also be coupled to devices such as, but not limited to, the implants illustrated in FIGS. 2, 17, and 21. By way of example, superior end member 4 of FIG. 11 is aligned with a medical implant 1*a* that has a length. The superior end member 4 is configured to interface with a skeletal structure at the end of its length through spikes 31, in the illustrated example, and by bearing of its various components against the skeletal structure. The superior end member 4 includes an end cap 30 with a thickness that provides connection to the medical implant 1*a* and connection to the skeletal structure, and a shoe 40. The shoe 40 attaches to the end cap 30 and spans at least a portion of an end cap opening 35. The shoe 40 provides at least in part an interface with the skeletal structure.

The end cap 30 may be a separate component, as illustrated, or may be integrated with an implant such as the medical implant 1*a*. The end member 4 in total and the end cap 30 may be of a uniform thickness, as shown in FIG. 11, or one or both of the end member 4 and the end cap 30, 30*a* may vary in thickness, as shown in FIG. 5, such that placement of the end member 4 on the medical implant 1 creates an interface with the implant 1 that is not parallel to the length of the implant 1. This non-parallel configuration may enable the end member 4 and the medical implant 1 to match the natural angles of a spinal curvature. For example, in much of the cervical and lumbar regions of the spine, the natural curvature is a lordotic angle. In much of the thoracic region of the spine, the natural curvature is a kyphotic angle.

As shown in FIG. 11, the superior end cap 30 includes a number of surface irregularities that may aid connection or interface with the skeletal structure. The surface irregularities illustrated are spikes 31 that are sharp to penetrate the skeletal structure. In other embodiments, the surface irregularities may be raked or straight teeth that tend to bite into the skeletal structures to resist expulsion in particular directions, such as, for example, to resist expulsion opposite to the path of insertion. The surface irregularities may be a surface finish, sprayed coating, or mechanical or chemical etching. The surface irregularities may be fixed, or may retract and deploy into a position to engage the skeletal structures.

The end cap 30 shown includes cap connectors 42 for coupling the end cap 30 to the medical implant 1*a*. The cap connectors 42 shown are round pins, but in other embodiments could be other shapes and could include other functions. For example, the cap connectors 42 may be square in cross-section or any other geometric shape. The cap connectors 42 may be oblong for sliding in slots into which they could be engaged, or may have hooked ends to grasp or otherwise capture a portion of the medical implant 1*a* when coupled. The implant 1*a* of FIG. 11 includes sliced opening 43 along with other openings for receiving the cap connectors 42. The sliced opening 43 includes a cut 44 that creates a flexible, living hinge capable of securely receiving one of the cap connectors 42. When a cap connector 42 is pushed into the sliced opening 43, the sliced opening 43 deforms to open and allows the cap connector 42 to slide into the sliced opening 43. After the cap connector 42 is seated in the sliced opening 43, the material returns to its pre-insertion position and creates a locking effect around the cap connector 42. In addition, or in the alternative, the cap connectors 42 may include relief cuts through some or all of their cross section to provide a living hinge or spring effect when inserted into an appropriately sized opening.

As illustrated in FIGS. 5 and 11, each of the end caps 30, 30a has eight equally radially spaced cap connectors 42. This spacing allows for the rotational orientation of the end caps 30, 30a to be altered at forty-five degree increments relative to the tubular members. The adjustable rotational orientations enable implants with end caps of varying thicknesses, such as end cap 30a, to be placed from substantially any surgical approach and simultaneously properly match the skeletal structures. For example, to match lordotic or kyphotic spinal angles while approaching from any of anterior, antero-lateral, posterior, postero-lateral, transforaminal, and far lateral approaches. Multiples other than eight may be used in various embodiments, and embodiments with spacing that is not equal may be employed to limit or direct orientation possibilities. The cap connectors 42 illustrated are part of the end caps 30, 30a, but in other embodiments, cap connectors may extend from the implants 1, 1a, 100, or 200, and be connectable to openings in respective end caps.

Figure 13:
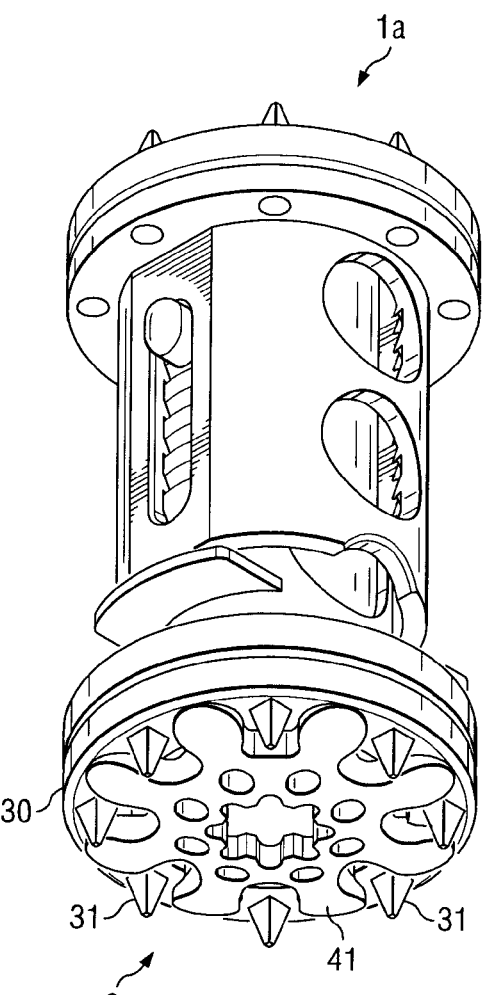
FIG. 13 is a perspective view of the implant of FIG. 11.

FIGS. 5 and 11 illustrate a superior shoe 40 that is concavely shaped relative to the end members 30, 30a. In some embodiments, this configuration may be advantageous because it provides for a small basket area in the central portion o the superior shoe 40. The basket area may be useful in receiving a portion of bone growth material that can be held directly against an endplate, or may be useful in matching and supporting certain anatomical structures. An inferior shoe 41 is shown in FIGS. 5 and 13 that is convexly shaped relative to the end members 30, 30a. This shape may be useful for a number of purposes, including matching and supporting adjacent anatomical structures. Although the inferior shoe 41 is illustrated as convex, and the superior shoe 40 is concave, note that either shape may be on either end of the medical implant, or only shapes of one type or the other only may be a part of the medical implant. Shoes of other shapes such as, but not limited to, flat may also be used.

In some embodiments, the superior and inferior shoes, 40, 41 may be made at least in part from a bioresorbable material. A bioresorbable material provides initial support and an initial containment structure for grafting material that may be placed within the implant. However, over time, the material dissolves and/or the body removes and replaces the material with tissue structures such as bone, thereby providing an especially open pathway through the implant for tissue growth. Examples of bioresorbable materials that could be incorporated in the superior and inferior shoes 40, 41, include but are not limited to allograft, autograft, and xenograft bone materials, polylactide, polyglycolide, tyrosine-derived polycarbonate, polyanhydride, polyorthoester, polyphosphazene, calcium phosphate, hydroxyapatite, bioactive glass, and combinations thereof.

In other embodiments, the superior and inferior shoes 40, 41 may be at least in part a bioactive substance proportioned to provide a clinical benefit to the recipient of the implant. Bioactive substances include but are not limited to antibiotics or other substances that affect infection, bone growth and bone ingrowth promoting substances, substances that treat or attack cancer cells, or any other substance that makes a therapeutic contribution.

The superior and inferior shoes 40, 41 include shoe connectors 47 for coupling the shoes 40, 41 to the end caps 30, 30a. The shoe connectors 47 shown are round pins, but in other embodiments could be other shapes and could include other functions. For example, the shoe connectors 47 may be square in cross-section or any other geometric shape. The shoe connectors 47 may be oblong for sliding in slots into which they could be engaged, or may have hooked ends to grasp or otherwise capture a portion of the end caps 30, 30a when coupled. The end caps 30, 30a may include sliced openings similar to those described in association with the sliced openings 43 described above. In addition, or in the alternative, the shoe connectors 47 may include relief cuts through some or all of their cross-section to provide a living hinge or spring effect when inserted into an appropriately sized opening.

Figure 12:
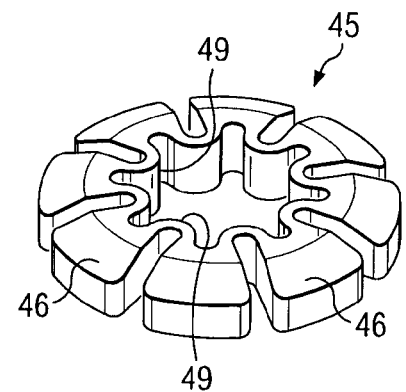
FIG. 12 is a perspective view of an embodiment of an end shoe.

FIG. 12 shows a compliant shoe 45 with shoe splines 46 that support shoe connectors (not shown) consistent with the shoe connectors 47 described herein. Between the shoe splines 46 with shoe connectors are shoe hinges 49. The shoe hinges 49 may provide living hinges between the shoe splines 46. In other embodiments, the shoe hinges 49 may be mechanical hinges or may be another material or a differently processed material. The hinged configuration permits the compliant shoe 45 to deform both angularly and radially in response to loading. Consequently, the implant is less likely to develop local areas of high stress. The shoe connectors of the compliant shoe 49 may also be more easily snapped into place as a result of the flexible characteristics of the device. Loading among the shoe connectors may be more easily distributed as a result of the properties of the compliant shoe 45.

Figure 17:
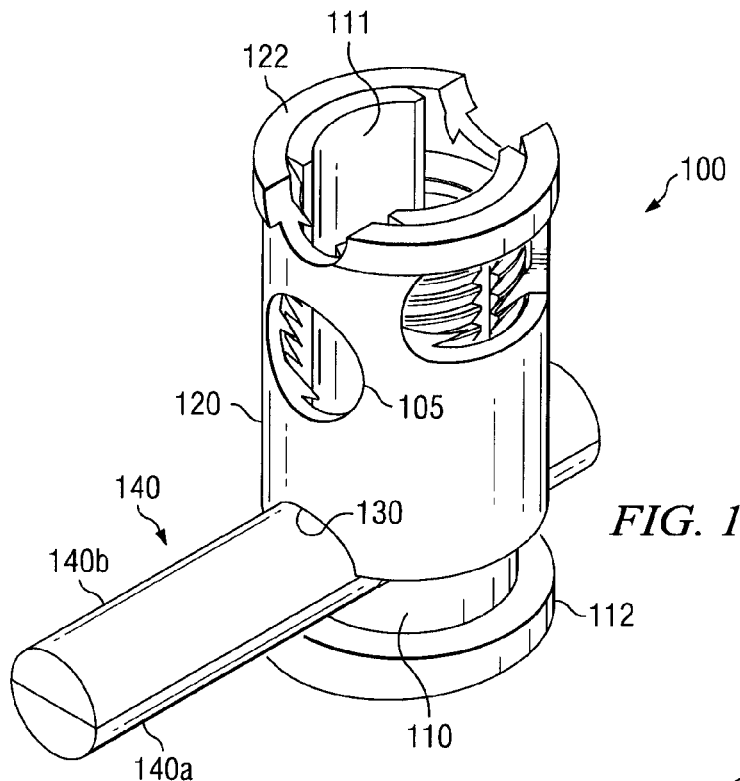
FIG. 17 is a perspective view of another expandable implant embodiment and a portion of an attached instrument.
Figure 18:
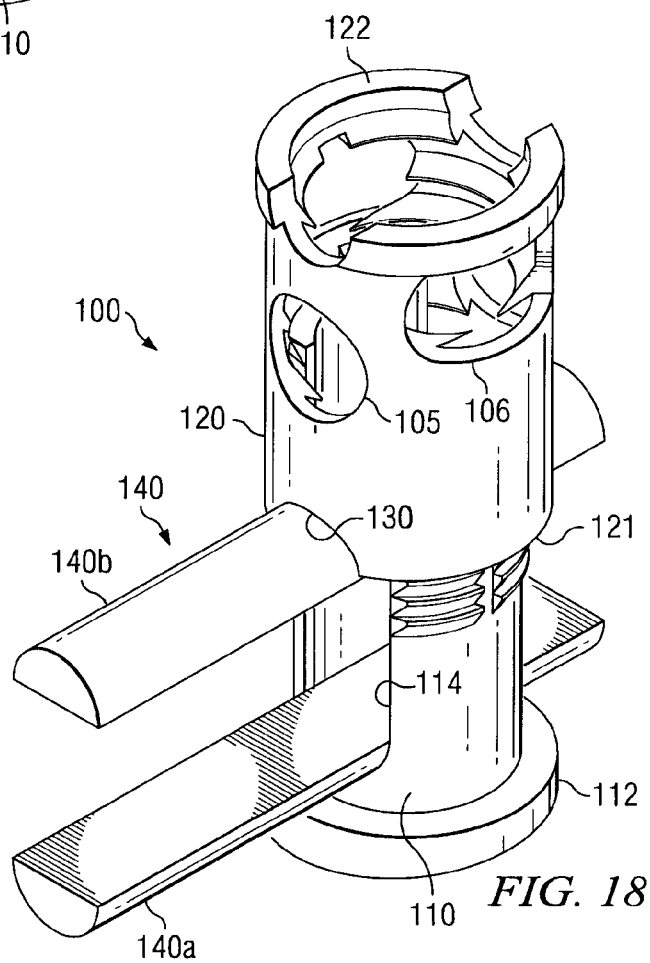
FIG. 18 is a perspective view of the implant and instrument of FIG. 17 in a more expanded state.

FIGS. 17 and 18 illustrate an expandable medical implant 100 for supporting skeletal structures, the expandable medical implant 100 having a length along its expandable dimension. In the illustrated embodiment, the expandable medical implant 100 includes a first tubular member 110 with a connection end 111, an opposite first skeletal interface end 112, and a central expansion instrument opening 114. In the embodiment shown, the central expansion instrument opening 114 is substantially on the lateral centerline of the first tubular member 110. This is beneficial in some embodiments to provide a central axis along which to expand the expandable medical implant 100. A central lifting point avoids eccentricities that may be generated by lifting from points beyond the central axis. In other embodiments, the central expansion instrument opening 114 may be beyond the central axis, although remaining within the periphery of the first tubular member 110.

The expandable medical implant 100 shown also includes a second tubular member 120 with a connection end 121 configured to engage with the connection end 111 of the first tubular member 110 by fitting within the second tubular member 120. In other embodiments, the first and second tubular members 110, 120 may partially interdigitate or may have a side-by-side alignment, or other configuration. The second tubular member 120 has an opposite second skeletal interface end 122. The embodiment shown includes a bone growth packing aperture 105 through which bone growth material may be packed and through which bone growth may occur. Additionally, the bone growth packing aperture 105 is an aid in radiographic assessment when the expandable medical implant 100 is made from a material that is not radiolucent. Lateral openings 106 may be useful for packing of bone growth material, and provide channels through which bone growth and radiographic assessment may occur.

The term tubular as used herein includes generally cylindrical members as are illustrated in FIGS. 17-18, but may also include other enclosed or partially enclosed cross-sectional shapes. By way of example and without limitation, tubular includes fully or partially, cylindrical, elliptical, rectangular, square, triangular, semi-circular, polygonal, and other cross-sectional shapes of these general types.

As illustrated in FIGS. 17 and 18, the combined first and second tubular members, 110, 120 are of a greater dimension along the length of the expandable medical implant 100 than the combined first and second tubular members 110, 120 are in any dimension perpendicular to their length. This aspect ratio may be particularly useful in replacing long structures that may be best accessed through narrow approaches or openings.

Embodiments of the invention may also include an expansion instrument insertable through the central expansion instrument opening 114. The insertion end 140 of such an expansion instrument is illustrated in FIGS. 17 and 18. The expansion instrument insertion end 140 shown has a lower segment 140a and an upper segment 140b. The lower segment 140a is expandable against the first tubular member 110, and the upper segment 140b is expandable against the second tubular member 120 to expand the medical implant 100. The lower and upper segments 140a, 140b shown are semi-circular in cross-section, but may be of any operable shape. Such shapes may be selected to provide improved insertion of the insertion end 140 into a patient or into an expandable medical implant 100, or may be selected for lifting, bearing, bending or shearing strength, or other characteristics.

Figure 20:
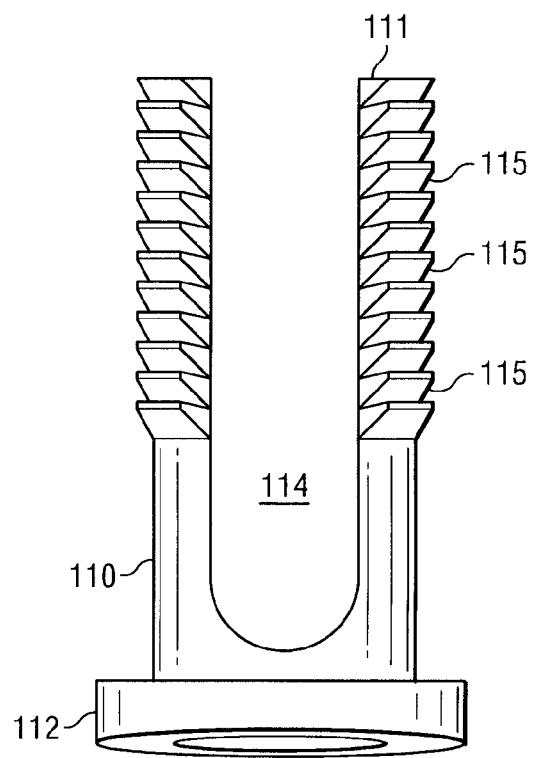
FIG. 20 is an elevation view of a component of the implant of FIG. 17.

As shown in FIGS. 18 and 20, the first tubular member 110 includes the central expansion instrument opening 114, which also serves as a relief cut to facilitate portions of the first tubular member 110 flexing away from the second tubular member 120 to permit translation between the first and second tubular members. The flexing may be induced by pushing the first tubular member 110 away from the second tubular member 120 as described above to expand the implant 100. In other embodiments, the central expansion instrument opening 114 may be closed near the connection end 111 of the first tubular member 110 and not facilitate the flexing function illustrated.

In other embodiments, a relief cut in the second tubular member 120 and a continuous shape in the first tubular member 110 could cause flexing of the second tubular member 120 rather than the first tubular member 110. Similarly, the degree and direction of flexing can be controlled by the use of different materials, various degrees of relief cutting, different cross-sectional shapes, and the shapes of the teeth or protrusions employed, among other factors. The force required for various degrees of flexing of the members is also proportional to the force required to expand the implant. Therefore, the force required to expand the implant may be maintained within a desirable range by controlling the factors detailed above.

Figure 19:
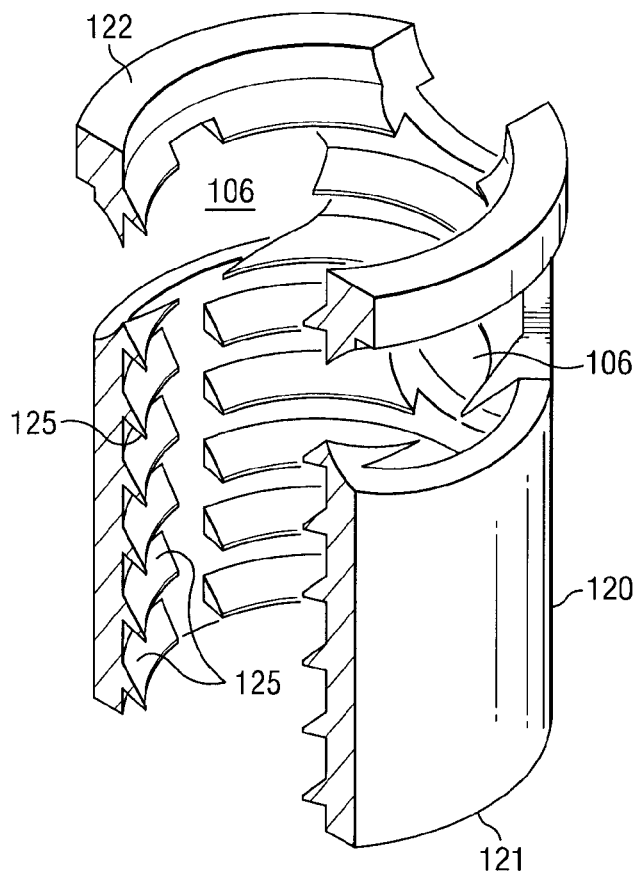
FIG. 19 is a partially cut away perspective view of a component of the implant of FIG. 17.

As best illustrated in FIGS. 19 and 20, the first tubular member 110 includes a set of first teeth 115, or more generally, protrusions, wherein each of the rows of teeth are adjacent to one another. The second tubular member 120 includes a set of second teeth 125, or more generally, protrusions, wherein the rows of teeth are not adjacent to one another. As shown, every other row of the set of second teeth 125 has been removed. However, in other embodiments, every third or fourth or some other member of rows may contain teeth, or the tooth pattern may repeat in some non-uniform fashion. If the sets of teeth were threads instead, a similar effect could be achieved by widening the pitch of the threads on one of the tubular members.

The first set of teeth 115 interdigitate with every other one of the teeth of the set of second teeth 125. This or other varied spacings may be advantageous. As noted above, the force required to expand the implant is proportional to the number of sets of teeth that are in contact while the tubular members 110, 120 are being translated. However, if teeth on both tubular members are spaced apart at greater distances, the number of increments to which the implant may be adjusted is decreased. By maintaining the frequency of the rows of the first set of teeth 115 and increasing frequency of the second set of teeth 125, the force required to expand the implant is reduced, but the number of discrete points of adjustment is not reduced. In some embodiments, the increased frequency of teeth could be maintained on the second tubular member 120 while the spacing is increased on the first tubular member 110.

In some embodiments, the second tubular member 120 includes an instrument aperture 130 for receiving at least a portion of the expansion instrument insertion end 140. Such an instrument aperture may provide for stability between the expansion instrument insertion end 140 and the expandable medical implant 100 and may provide for additional space through which to place the insertion end 140, among other purposes.

As illustrated in FIGS. 17 and 18, the width of the insertion end 140 of the expansion instrument is less than one half of the width of either of the first or second tubular members 110, 120. For the purpose of describing the width of the insertion end 140 relative to the tubular members 110, 120, the width is a dimension perpendicular to the length of the expandable medical implant 100. The width of the insertion end 140 and the first or second tubular members 110, 120, should be considered in the same plane for the purpose of comparison. In some embodiments, a relatively narrow insertion end 140 is useful to facilitate visualization of the surgical site while placing the expandable medical implant 100. A relatively small insertion end 140 may also be valuable to reduce the size of the required surgical incision.

In some embodiments, the expandable medical implant may also include a bone growth promoting substance. The use of such substances is described in more detail below.

Some embodiments associated with implant 1, 1a, 100, and 200 may also include supplemental fixation devices as part of the expandable medical implant for further stabilizing the anatomy. For example, and without limitation, rod and screw fixation systems, anterior or lateral plating systems, facet stabilization systems, spinal process stabilization systems, and any devices that supplement stabilization may be used as a part of the expandable medical implant.

Embodiments of the invention are generally for supporting skeletal structures, and may include an expandable implant with a first tubular member and a second tubular member. The expandable implant of some embodiments includes a means for receiving an expansion instrument. The means for receiving an expansion instrument may be an aperture or apertures of any type, may be a protrusion or protrusions of any type, may include a friction interface, or any other mechanism designed to transfer force from the expansion instrument to the implant. The expansion instrument means is for expanding against the first tubular member and the second tubular member to expand the implant. The instrument means may include device sufficient to separate the first and second tubular members.

The expansion instrument means of some embodiments is centrally located on the expandable implant such that when the expandable implant is placed in a person to support the skeletal structures with the expansion instrument means attached. Ends of the expandable implant that interface with the skeletal structure may be viewed from the direction of insertion of the expandable implant. In some of these and other embodiments, lateral extents of the expandable implant are also viewable from the direction of insertion of the expandable implant. The term lateral extents is intended to include segments of the expandable implant such as lateral openings 106 that are located on or near edges of the expandable implant that are transverse to the insertion direction of the implant.

An embodiment of the invention is a method of placing an expandable vertebral body replacement device such as expandable medical implant 100 shown in FIGS. 17 and 18. Embodiments may include making an incision adjacent to a vertebral body and removing at least a portion of the vertebral body.

As shown in FIG. 17, the expandable medical implant 100 is placed on an insertion end 140 of an expansion instrument in a contracted position. In the contracted position, the insertion end 140 of the expansion instrument is configured to pass through a central portion of the expandable medical implant 100, such as the central expansion instrument opening 114, without extending onto any surface of the expandable medical implant 100 that is lateral to an insertion direction. For example, the insertion end 140 does not extend onto a lateral extent or either of the skeletal interface ends 112, 122.

Embodiments of the method may further include inserting the expandable medical implant 100 at least in part into a volume left open after removal of the portion of the vertebral body, expanding the expansion instrument to secure the expandable medical implant 100, and removing the expansion instrument through the incision. Some embodiments may also include placing bone growth promoting substance within the expandable medical implant 100 prior to expansion of the expandable medical implant 100. Further, in some embodiments, bone growth promoting substance may additionally or lieu be placed within the expandable medical implant 100 after expansion of the expandable medical implant 100.

Additional fixation devices to supplement the fixation of the vertebral body replacement may be added to the construct in some circumstances. Suitable supplemental fixation devices are described herein and include others that provide a clinical benefit.

FIGS. 21-26 illustrate another embodiment of the invention. An expandable medical implant 200 with a length along its expandable dimension is shown. The medical implant 200 is for supporting skeletal structures and has a first tubular member 210 with a connection end 211, including a first set of protrusions 215. The first tubular member 210 shown has an opposite skeletal interface end 212. The medical implant 200 includes a second tubular member 220 with a connection end 221 including a second set of protrusions 225 configured to engage with the connection end 211 of the first tubular member 210. The second tubular member 220 includes an opposite end 222 opposite from the connection end 221.

FIG. 23 illustrates the expandable implant 200 with a third tubular member 230. The third tubular member 230 shown has a connection end 231 including a third set of protrusions 235 configured to engage with the opposite end 222 of the second tubular member 220. The second tubular member 220 includes a fourth set of protrusions 227 on the opposite end 222. In some embodiments, the first and third tubular member 210, 230, are configured to fit within the second tubular member 220.

Figure 25B:
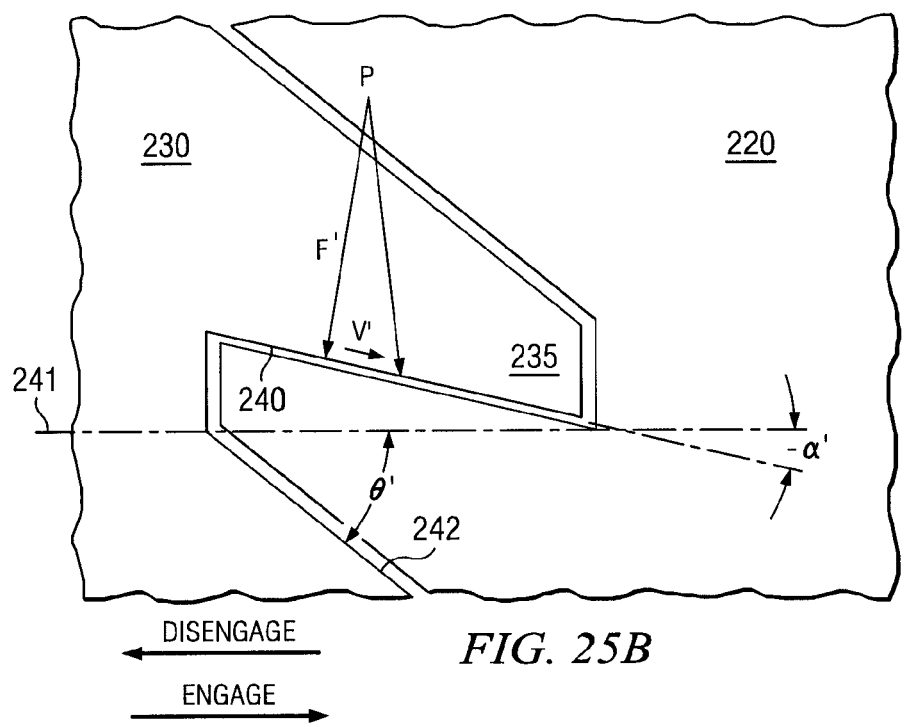
FIG. 25B is a cross-sectional view of protrusions of an embodiment of the implant of FIG. 21.

As shown in FIGS. 24 and 25B for the third set of protrusion 235, one or both of the first and third sets of protrusions 215, 235 have a flank 240 with a negative flank angle $-\alpha'$. For the purpose of illustration, only the third set of protrusions 235 is being described in detail, but the same or directly correlating relationships may be applied to the first set of protrusions 215 of FIG. 26.

The term "flank" as used herein is the thread face, excluding any crest or root of the thread profile. The term "flank angle" as used herein is the angle between the individual flank and a perpendicular 241 to the axis of the thread measured in the axial plane. As shown, the axis of the thread is parallel with the length of the expandable implant 200. As an example, the sets of protrusions will be described as a thread embodiment, but the protrusions in other embodiments may be notches or ratchetings of any operable type.

FIGS. 25A and 25B show a comparison between a typical prior art thread profile and a thread profile having a negative flank angle. Both profiles include the perpendicular 241 to the length of the expandable implant 200. A load applied as a compression force to an expandable implant 200 would be transferred to the interface between the threads in some proportion as shown in FIGS. 25A and 25B, the force being designated as P herein. An upper flank 260 and a lower flank 262 are shown for the prior art thread profile with flank angles of $\alpha$ and $\theta$ respectively. Resolved as forces along the flank 260, the force P is a force normal to the flank F, and a shear force along the flank V. For reference, arrows designating the results of applying lateral forces to the third tubular member 230 are provided in FIGS. 25A and 25B. A force applied to the left will tend to disengage the threads, and a force applied to the right will tend to engage the threads.

As seen with reference to FIG. 25A, the normal force F is directed into the engaged, opposing flank and the shear force V tends to push a prior art member in the position of the third tubular member 230 along the flank 260. A resultant of the shear force V therefore tends to disengage the threads. This tendency to disengage may be heightened with devices that are designed to expand or contract to flex over other component parts while expanding. For example, as shown in FIG. 23, the third tubular member 230 must flex inwardly to move linearly relative to the second tubular member 220 and thus to expand. Analysis along the lower flank 262 is unnecessary because compressive forces applied to an implant in this configuration tend to separate, not engage the lower flank 262.

FIG. 25B illustrates an upper flank 240 and a lower flank 242 with flank angles of $-\alpha'$ and $\theta'$ respectively. Resolved as forces along the flank 240, the force P is a force normal to the flank F', and a shear force along the flank V'. The normal force F' is directed into the engaged, opposing flank and the shear force V' tends to push the third tubular member 230 along the flank 240. A resultant of the shear force V' therefore tends to engage the threads as the flank 240 is positively loaded by compressive force on the expandable implant 200. Analysis along the lower flank 242 is unnecessary because compressive forces applied to the expandable implant 200 tend to separate, not engage the lower flank 242.

In a device such as expandable implant 200, maintenance of the implant height under compressive load requires that the protrusions of the tubular members stay engaged with one another. The negative flank angle protrusions illustrated in FIG. 25B contribute to the effectiveness and stability of an implant. Although shown with reference to the expandable implant 200, negative flank angle protrusions may also be applied to expandable medical implants 1, 1a, and 100. Zero degree flank angles are also known, but do not provide the positively engaging force of the negative flank angle embodiments.

Embodiments of the invention as described in relation to FIGS. 21-26 result in implants that, when compressively loaded along the length of the implants, generate compressive force between the engaged tubular member transverse to the length of the implant. As noted, these force tending to more securely engage the sets of protrusions supporting the implants.

Figure 22:
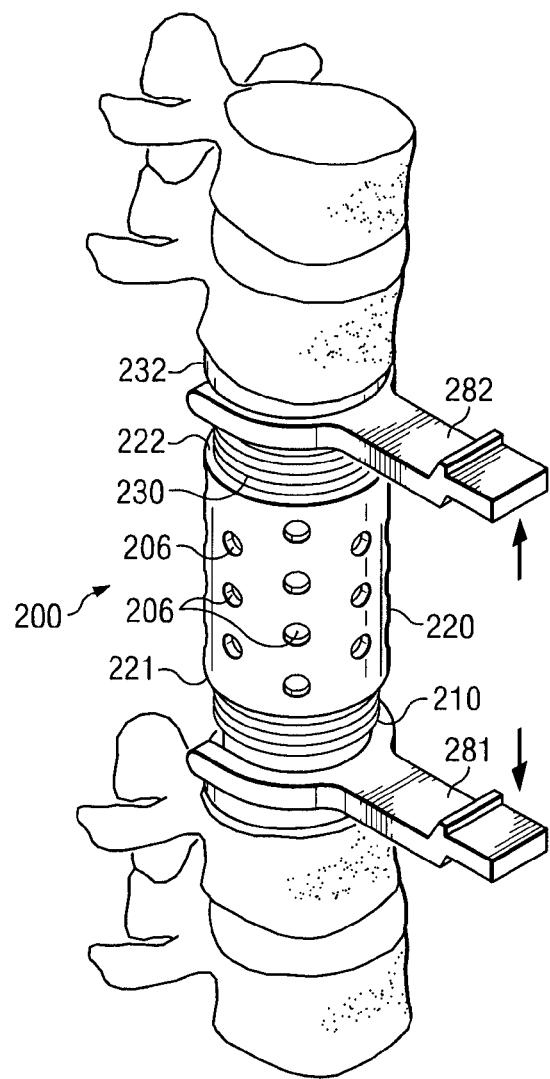
FIG. 22 is a perspective view of the implant and instrument of FIG. 21 in a more expanded state.

The term tubular as used herein includes generally cylindrical members as are illustrated in FIG. 22, but may also include other enclosed or partially enclosed cross-sectional shapes. By way of example and without limitation, tubular includes fully or partially, cylindrical, elliptical, rectangular, square, triangular, semi-circular, polygonal, and other cross-sectional shapes of these general types.

In alternate embodiments, the opposite end 222 may be configured to be a skeletal interface end, rather than connecting to a third tubular member.

Figure 26:
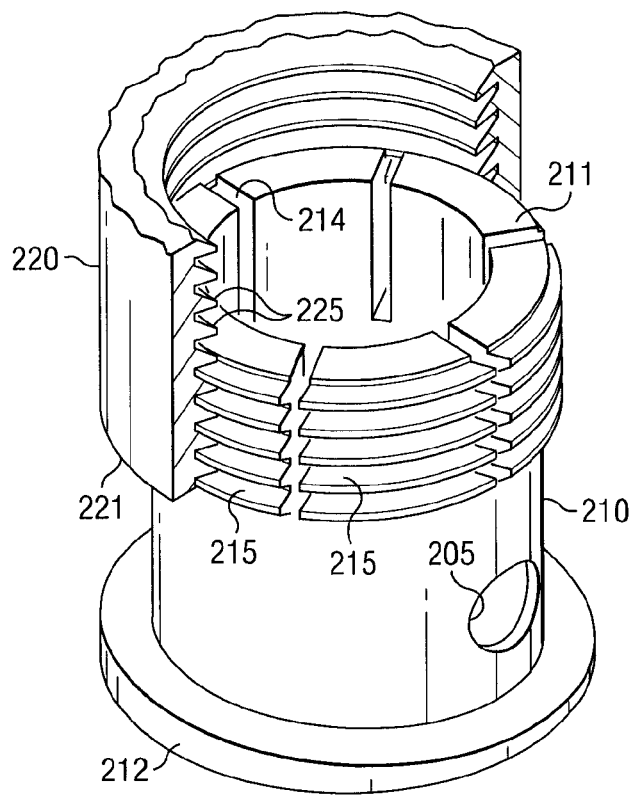
FIG. 26 is perspective view the inferior end of the implant of FIG. 21 with a partially cut away section.

As shown in FIG. 26, the first tubular member 210 includes a relief cut 214 to facilitate portions of the first tubular member 210 flexing away from the second tubular member 220 to permit translation between the first and second tubular members 210, 220. The flexing may be induced by pulling the first tubular member 210 away from the second tubular member 220 to expand the implant 200. In other embodiments, a relief cut in the second tubular member 220 and a continuous shape in the first tubular member 210 could cause flexing of the second tubular member 220 rather than the first tubular member 210. Similarly, the degree and direction of flexing can be controlled by the use of different materials, various degrees of relief cutting, different cross-sectional shapes, and the shapes of the teeth or protrusions employed, among other factors. The force required for various degrees of flexing of the members is also proportional to the force required to expand the implant. Therefore, the force required to expand the implant may be maintained within a desirable range by controlling the factors detailed above. Similarly, the third tubular member 230 may be configured to include one or more relief cuts 224 (FIG. 23) to facilitate portions of the third tubular member flexing away from the second tubular member to permit translation between the third and second tubular members, and may be the outer rather than the inner member.

As described above with regard to the protrusions of FIGS. 3 and 4, the sets of protrusions of the first, second, and third tubular members 210, 220, 230 may include adjacent spacing and non-adjacent spacing in various embodiments.

The implant FIGS. 23 and 26 includes apertures 205 in the first and third tubular members 210, 230 through which bone growth material may be packed and through which bone growth may occur. Additionally, the apertures 205 aid in radiographic assessment when the implant 200 is made from a material that is not radiolucent. Openings 206 (FIGS. 21 and 22) in the second tubular member 220 are also useful for packing of bone growth material, and provide channels through which bone growth may occur.

Figure 21:
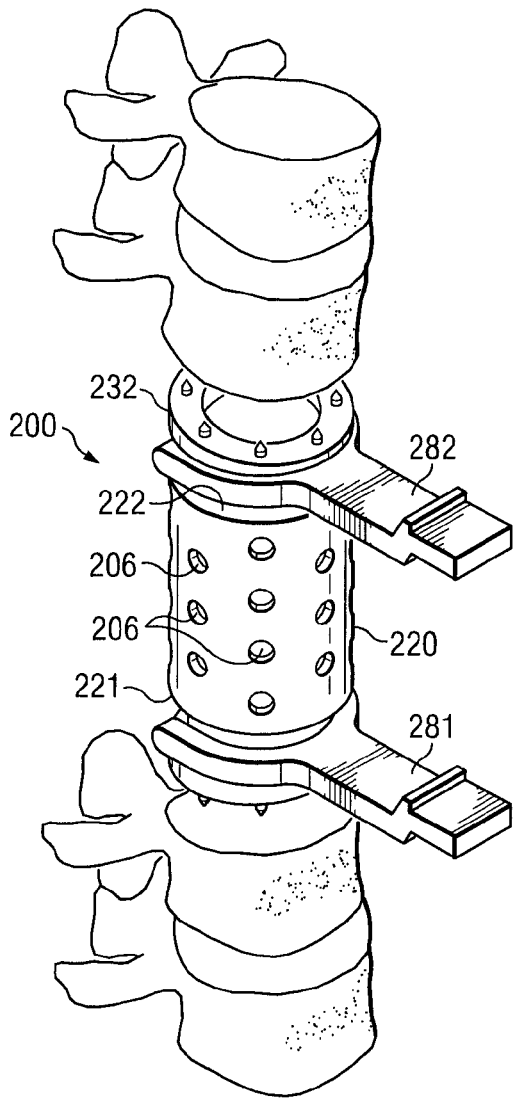
FIG. 21 is a perspective view of another expandable implant embodiment and a portion of an attached instrument between vertebrae.

Embodiments of the invention include an insertion instrument with a lower tip 281 and an upper tip 282, as illustrated in FIGS. 21 and 22. Acceptable devices for driving the lower and upper tips 281, 282 are disclosed in detail above in association with instruments applied to implants 1, 1a, and 100. In addition, some embodiments may include devices for rotating the second tubular member 220. This rotation may be achieved by inserting a rod or driver into one or more of the openings 206 and rotating the second tubular member 220 relative to the first and/or second tubular members 210, 230. In addition, rotation of the second tubular member 220 may be accomplished by devices such as are disclosed in U.S. patent application Ser. No. 10/663,554, entitled, "Expansion Tool for Adjustable Spinal Implant" filed Sep. 16, 2003, which is hereby incorporated by reference in its entirety, or any other device for effectively rotating the tubular members 210, 220, and 230.

An embodiment of the invention is an expandable medical implant 200 with a length along its expandable dimension, the medical implant 200 for supporting skeletal structures. The embodiment includes a first tubular member 210 with a connection means and a second tubular member 220 with a connections means for coupling with the first tubular member. A means for translating the first tubular member 210 relative to the second tubular member 220 to provide coarse expansion adjustment is provided along with a means for providing fine length adjustment by turning the second tubular member 220 relative to the first tubular member 210. As illustrate in FIGS. 21-26, the course expansion adjustment means is provided by separating the lower and upper tips 281, 282 with an insertion instrument, and the fine adjustment means is accomplished by rotating the second tubular member 220 as disclosed above. Other configurations for the course expansion are contemplated, such as those disclosed in relation to implants 1, 1a, and 100. For embodiments of implants 1, 1a, and 100 to include the fine adjustment capability, the protrusions of those embodiments could include inclined threads or other devices that produce expansion in response to rotation.

An embodiment of the invention is a method of implanting an implant, such as expandable medical implant 200. The expandable medical implant 200 has a length along the expandable dimension of the implant. The method may include pulling a first tubular member 210 with a first set of protrusions 215, or in some embodiments, threads, away from a second tubular member 220 with a second set of protrusions 225, or in some embodiments threads, causing the first and second sets of protrusions 215, 225 to translate relative to one another along the length of the implant. Further, in some embodiments, turning the second tubular member 220 relative to the first tubular member 210 adjusts the length of the expandable medical implant 200.

Another method embodiment is also directed to implanting an expandable medical implant with a length along the expandable dimension of the implant. An implant such as expandable medical implant 200 may be expanded by pulling a first tubular member 210 with a first set of protrusion 215 away from a third tubular member 230 with a fourth set of protrusions 235. In this embodiment, the first set of protrusions 215 is a set of right-hand threads and the fourth set of protrusions 235 is a set of left-hand threads. The expandable medical implant 200 also includes a second tubular member 220 with a second set of protrusions 225 and a third set of protrusions 227. In this embodiment, the second set of protrusions 225 is a set of right-hand threads and the third set of protrusions 227 is a set of left-hand threads.

The act of pulling noted above may cause the first and second sets of protrusions, 215, 225, or threads, to translate relative to one another along the length of the implant 200. Similarly, the act of pulling may cause the third and fourth sets of protrusions, 227, 235, or threads, to translate relative to one another along the length of the implant 200. In some embodiments, turning the second tubular member 220 relative to the first and third tubular members 210, 230 will adjust the expanded length of the expandable medical implant 200. Turning in a first direction will cause shortening of the expandable medical implant 200, and turning in an essentially opposite direction will cause lengthening of the expandable medical implant 200. For example, turning the second tubular member 220 clockwise shortens the expandable medical implant 200, and turning the second tubular member 220 counter-clockwise lengthens the expandable medical implant 200.

Various method embodiments of the invention are described herein with reference to particular implants 1, 1a, 100, and 200. However, in some circumstances, each disclosed method embodiment may be applicable to each of the implants 1, 1a, 100, and 200, or to some other implant operable as disclosed with regard to the various method embodiments.

In some circumstances, it is advantageous to pack all or a portion of the interior and/or periphery of the implants 1, 1a, 100, 200 with a suitable osteogenic material or therapeutic composition. Osteogenic materials include, without limitation, autograft, allograft, xenograft, demineralized bone, synthetic and natural bone graft substitutes, such as bioceramics and polymers, and osteoinductive factors. A separate carrier to hold materials within the device may also be used. These carriers may include collagen-based carriers, bioceramic materials, such as BIOGLASS®, hydroxyapatite and calcium phosphate compositions. The carrier material may be provided in the form of a sponge, a block, folded sheet, putty, paste, graft material or other suitable form. The osteogenic compositions may include an effective amount of a bone morphogenetic protein (BMP), transforming growth factor β1, insulin-like growth factor, platelet-derived growth factor, fibroblast growth factor, LIM mineralization protein (LMP), and combinations thereof or other therapeutic or infection resistant agents, separately or held within a suitable carrier material. A technique of an embodiment of the invention is to first pack an unexpanded implant, as shown in FIGS. 14A and 14B, with material and then place one or both end members if desired. Upon expanding the device to an expanded state such as is shown in FIG. 2, material may additionally be placed through the medial aperture 5 and/or openings 6. Placement may be accomplished directly or with the aid of an injection or transfer device of any effective type. Such a technique may be practiced for implants 1, 1a, 100, and 200 as well.

Embodiments of the implant in whole or in part may be constructed of biocompatible materials of various types. Examples of implant materials include, but are not limited to, non-reinforced polymers, carbon-reinforced polymer composites, PEEK and PEEK composites, shape-memory alloys, titanium, titanium alloys, cobalt chrome alloys, stainless steel, ceramics and combinations thereof. If the trial instrument or implant is made from radiolucent material, radiographic markers can be located on the trial instrument or implant to provide the ability to monitor and determine radiographically or fluoroscopically the location of the body in the spinal disc space. In some embodiments, the implant or individual components of the implant are constructed of solid sections of bone or other tissues. In other embodiments, the implant is constructed of planks of bone that are assembled into a final configuration. The implant may be constructed of planks of bone that are assembled along horizontal or vertical planes through one or more longitudinal axes of the implant. Tissue materials include, but are not limited to, synthetic or natural autograft, allograft or xenograft, and may be resorbable or non-resorbable in nature. Examples of other tissue materials include, but are not limited to, hard tissues, connective tissues, demineralized bone matrix and combinations thereof. Examples of resorbable materials that may be used include, but are not limited to, polylactide, polyglycolide, tyrosine-derived polycarbonate, polyanhydride, polyorthoester, polyphosphazene, calcium phosphate, hydroxyapatite, bioactive glass, and combinations thereof. Implant may be solid, porous, spongy, perforated, drilled, and/or open.

FIG. 1 illustrates four vertebrae, $V_1$-$V_4$, of a typical lumbar spine and three spinal discs, $D_1$-$D_3$. While embodiments of the invention may be applied to the lumbar spinal region, embodiments may also be applied to the cervical or thoracic spine or between other skeletal structures.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. An expandable medical implant for supporting skeletal structures comprising:
   a first tubular member having a generally cylindrical configuration with a first connection end and an opposite first skeletal interface end and a first longitudinal axis extending between the first connection end and the first skeletal interface;
   a second tubular member having a generally cylindrical configuration with a second connection end configured to engage with the first connection end of the first tubular member, the second tubular member having an opposite second skeletal interface end and a second longitudinal axis extending between the second connection end and the second skeletal interface, an elongated slot extending through the second tubular member in a direction parallel to the second longitudinal axis; and
   a key pin non-threadingly fixedly secured to the first tubular member and extending outward from an outer surface of the first tubular member, the key pin positioned within the slot extending through the second tubular member such that engagement of the key pin and the slot guides translation between the first tubular member and the second tubular member along a desired path in a direction parallel to the first and second longitudinal axes without relative rotation of the first and second tubular members.

2. The expandable medical implant of claim 1, wherein the first tubular member is sized to be received within the second tubular member.

3. The expandable medical implant of claim 2, wherein the first tubular member includes a relief cut to facilitate portions of the first tubular member flexing away from the second tubular member to permit translation between the first and second tubular members.

4. The expandable medical implant of claim 3, wherein the key pin and the relief cut are oriented such that application of a force radially inward on the key pin causes inward flexing of the portions of the first tubular member away from the second tubular member to permit translation between the first and second tubular members.

5. The expandable medical implant of claim 3 wherein the first tubular member includes a first set of protrusions each comprising a flank oriented in a first direction and the second tubular member includes a second set of protrusions each comprising a flank oriented in a second direction, opposite the first direction.

6. The expandable medical implant of claim 5 wherein translation of the first tubular member relative to the second tubular member causes the flanks of the first set of protrusions to press against the flanks of the second set of protrusions such that force is induced between the flanks of the first set of protrusions to press against the flanks of the second set of protrusions causing the first tubular member to flex away from the second tubular member.

7. The expandable medical implant of claim 3 wherein the first tubular member includes a first set of protrusions and the second tubular member includes a second set protrusions, wherein each protrusion of the first set of protrusions interdigitates with every other protrusion of the second set of protrusions.

8. The expandable medical implant of claim 1 wherein the first tubular member includes a first set of adjacent protrusions that are spaced apart from one another by a first distance.

9. The expandable medical implant of claim 8 wherein the second tubular member includes a second set of protrusions that are spaced apart from one another by a second distance that is greater than the first distance, wherein one or more of the second set of protrusions interdigitate with one or more of the first set of adjacent protrusions.

10. The expandable medical implant of claim 9 wherein engagement of the key pin with upper and lower boundaries of the slot limit movement of the first tubular member relative to the second tubular member to a constrained range.

11. The expandable medical implant of claim 9, wherein the first and second sets of protrusions are shaped to allow expansion of the medical implant and resist compression of the medical implant.

12. An expandable medical implant for supporting one or more skeletal structures, comprising:
a first tubular member having a first body portion extending along a first axis, the first body portion having a first bone-engaging portion adjacent a first end and an opposing connection portion adjacent a second end, the connection portion comprising a plurality of external projections and at least one key pin non-threadingly fixedly secured to the first body portion and extending radially outward from the first body portion; and
a second tubular member movably engaged with the first tubular member, the second tubular member having a second body portion extending along the first axis, the second body portion having a plurality of internal projections mating with the plurality of external projections of the first tubular member and at least one slot extending through a side of the second body portion, the at least one slot receiving the at least one key pin of the first tubular member such that the mechanical engagement of the at least one key pin and the at least one slot guides translational movement between the first tubular member and the second tubular member along the first axis and prevents rotation of the first tubular member relative to the second tubular member, wherein engagement of the at least one key pin with a bottom portion of the at least one slot limits an expansion of the first and second tubular members.

13. The expandable medical implant of claim 12, wherein the first tubular member comprises at least one relief cut to facilitate portions of the first tubular member flexing away from the second tubular member to permit translational movement between the first and second tubular members without relative rotation between the first and second tubular members.

14. The expandable implant of claim 13, wherein the first tubular member comprises a pair of relief cuts positioned substantially opposite one another.

15. The expandable medical implant of claim 14, wherein the first tubular member comprises a pair of key pins positioned substantially opposite one another and wherein the second tubular member comprises a pair of slots positioned substantially opposite one another, the pair of slots of the second tubular member receiving the pair of key pins of the first tubular member.

16. The expandable implant of claim 12, wherein the at least one slot extends in a generally linear direction in a direction parallel to the first axis.

17. The expandable implant of claim 12, wherein engagement of the at least one key pin with an upper portion of the at least one slot limits a contraction of the first and second tubular members.

18. The expandable implant of claim 12, wherein at least the connection portion of the first tubular member is sized and shaped to be disposed within the second tubular member.

19. The expandable medical implant of claim 12, wherein the first tubular member comprises a pair of key pins positioned substantially opposite one another and wherein the second tubular member comprises a pair of slots positioned substantially opposite one another, the pair of slots of the second tubular member receiving the pair of key pins of the first tubular member.

20. The expandable medical implant of claim 12, wherein the plurality of external projections are spaced apart from one another by a first distance and the plurality of internal projections are spaced apart from one another by a second distance that is greater than the first distance.

* * * * *